US007176238B1

(12) United States Patent
Garvey et al.

(10) Patent No.: US 7,176,238 B1
(45) Date of Patent: Feb. 13, 2007

(54) NITROSTATED AND NITROSYLATED PROSTAGLANDINS, COMPOSITIONS AND METHODS OF USE

(75) Inventors: David S. Garvey, Dover, MA (US); Ricky D. Gaston, Malden, MA (US); L. Gordon Letts, Dover, MA (US); Inigo Saenz de Tejada, Madrid (ES); Sang William Tam, Dover, MA (US); Manuel Worcel, Boston, MA (US)

(73) Assignee: NitroMed Inc., Lexington, MA (US)

( * ) Notice: Subject to any disclaimer, the term of this patent is extended or adjusted under 35 U.S.C. 154(b) by 0 days.

(21) Appl. No.: 09/516,194

(22) Filed: Mar. 1, 2000

Related U.S. Application Data

(60) Provisional application No. 60/122,273, filed on Mar. 1, 1999, provisional application No. 60/138,502, filed on Jun. 9, 1999.

(51) Int. Cl.
*A61K 31/557* (2006.01)
*C07C 405/00* (2006.01)

(52) U.S. Cl. ..................... 514/530; 560/121
(58) Field of Classification Search ............... 560/121; 514/530
See application file for complete search history.

(56) References Cited

U.S. PATENT DOCUMENTS

| 3,922,293 | A | * | 11/1975 | Morozowich ............... 554/228 |
| 5,380,758 | A | | 1/1995 | Stamler et al. |
| 5,474,535 | A | | 12/1995 | Place et al. |
| 5,492,911 | A | | 2/1996 | Stief |
| 5,574,068 | A | | 11/1996 | Stamler et al. |
| 5,625,083 | A | * | 4/1997 | Bezuglov et al. ........... 549/467 |
| 5,648,393 | A | | 7/1997 | Stamler et al. |
| 5,708,031 | A | | 1/1998 | Scott |
| 5,718,917 | A | | 2/1998 | See |
| 5,769,088 | A | | 6/1998 | Place |
| 5,773,020 | A | | 6/1998 | Place et al. |
| 5,820,587 | A | | 10/1998 | Place |
| 5,877,216 | A | | 3/1999 | Place et al. |
| 5,886,039 | A | | 3/1999 | Kock et al. |
| 5,891,915 | A | | 4/1999 | Wysor et al. |
| 5,942,545 | A | | 8/1999 | Samour et al. |
| 5,962,528 | A | | 10/1999 | Scott |
| 5,981,593 | A | | 11/1999 | Scott |
| 6,013,277 | A | | 1/2000 | Curri |
| 6,031,002 | A | | 2/2000 | Wysor et al. |
| 6,037,346 | A | | 3/2000 | Doherty, Jr. et al. |
| 6,579,863 | B1 | * | 6/2003 | Garvey et al. ............... 514/171 |
| 6,593,347 | B2 | * | 7/2003 | Bandarage et al. ......... 514/327 |

FOREIGN PATENT DOCUMENTS

| EP | 0357581 | 3/1990 |
| EP | 0432199 | 6/1991 |
| EP | 0526566 | 2/1993 |
| WO | 9709049 | 3/1997 |
| WO | 9739760 | 10/1997 |
| WO | 9850039 | 11/1998 |
| WO | 9858910 | 12/1998 |
| WO | WO98/58910 | * 12/1998 |
| WO | 9902147 | 1/1999 |
| WO | 9902164 | 1/1999 |
| WO | 9920266 | 4/1999 |
| WO | 9921562 | 5/1999 |
| WO | 9922714 | 5/1999 |
| WO | 9922731 | 5/1999 |
| WO | 9930718 | 6/1999 |
| WO | 9956728 | 11/1999 |
| WO | 9956741 | 11/1999 |
| WO | 9965303 | 12/1999 |

OTHER PUBLICATIONS

Buvat et al, *The Journal of Urology*, 159:116-119 (1998).
Tordjman, *Contracept. Fertil. Sex.*, 21(6):509-510 (1993).
Porst, *The Journal of Urology*, 149:1280-1283 (1993).
Godschalk, *The Journal of Urology*, 151:1530-1532 (1994).
Hellstrom et al, *The Journal of Urology*, 151:1723-1727 (1994).
MacAllister et al, *The J. of Pharmac. and Exp. Ther.*, 273(1):154-160 (1995).
Gupta et al, *British Journal of Pharmacology*, 116:2201-2206 (1995).
Martinez-Pineiro et al, *The Journal of Urology*, 153:1487-1490 (1995).
Linet et al, *The New England Journal of Medicine*, 334(140:873-877 (1996).
Gambone et al, *British Journal of Pharmacology*, 121:271-279 (1997).
Bechara et al, *The Journal of Urology*, 157:2132-2134 (1997).
Porst, *Int. J. of Impotence Res.*, 9:187-192 (1997).
*Physician's Desk Reference*, p. 2458.

* cited by examiner

*Primary Examiner*—Laura L. Stockton
(74) *Attorney, Agent, or Firm*—Wilmer Cutler Pickering Hale and Dorr LLP

(57) ABSTRACT

The present invention describes novel nitrosated and/or nitrosylated prostaglandins, and novel compositions comprising at least one nitrosated and/or nitrosylated prostaglandin, and, optionally, at least one compound that donates, transfers or releases nitric oxide, elevates endogenous levels of endothelium-derived relaxing factor, stimulates endogenous synthesis of nitric oxide or is a substrate for nitric oxide synthase, and/or at least one vasoactive agent. The present invention also provides novel compositions comprising at least one prostaglandin and at least one S-nitrosothiol compound, and, optionally, at least one vasoactive agent. The prostaglandin is preferably a prostaglandin $E_1$ compound, more preferably alprostadil, and the S-nitrosothiol compound is preferably S-nitrosoglutathione. The present invention also provides methods for treating or preventing sexual dysfunctions in males and females, for enhancing sexual responses in males and females, and for treating or preventing cerebrovascular disorders, cardiovascular disorders, benign prostatic hyperplasia (BPH), glaucoma, peptic ulcers or for inducing abortions. The compounds and/or compositions of the present invention can also be provided in the form of a pharmaceutical kit.

4 Claims, 4 Drawing Sheets

NITROSTATED AND NITROSYLATED PROSTAGLANDINS, COMPOSITIONS AND METHODS OF USE

RELATED APPLICATIONS

This application claims priority to U.S. Provisional Application No. 60/122,273 filed Mar. 1, 1999 and U.S. Provisional Application No. 60/138,502 filed Jun. 9, 1999.

FIELD OF THE INVENTION

The present invention describes novel nitrosated and/or nitrosylated prostaglandins, and novel compositions comprising at least one nitrosated and/or nitrosylated prostaglandin, and, optionally, at least one compound that donates, transfers or releases nitric oxide, elevates endogenous levels of endothelium-derived relaxing factor, stimulates endogenous synthesis of nitric oxide or is a substrate for nitric oxide synthase, and/or at least one vasoactive agent. The present invention also provides novel compositions comprising at least one prostaglandin and at least one S-nitrosothiol compound, and, optionally, at least one vasoactive agent. The prostaglandin is preferably a prostaglandin $E_1$ compound, more preferably alprostadil, and the S-nitrosothiol compound is preferably S-nitrosoglutathione. The present invention also provides methods for treating or preventing sexual dysfunctions in males and females, for enhancing sexual responses in males and females, and for treating or preventing cerebrovascular disorders, cardiovascular disorders, benign prostatic hyperplasia (BPH), glaucoma, peptic ulcers or for inducing abortions. The compounds and/or compositions of the present invention can also be provided in the form of a pharmaceutical kit.

BACKGROUND OF THE INVENTION

Adequate sexual function is a complex interaction of hormonal events and psychosocial relationships. There are four stages to sexual response as described in the *International Journal of Gynecology & Obstetrics,* 51(3):265–277 (1995). The first stage of sexual response is desire. The second stage of sexual response is arousal. Both physical and emotional stimulation may lead to breast and genital vasodilation and clitoral engorgement (vasocongestion). In the female, dilation and engorgement of the blood vessels in the labia and tissue surrounding the vagina produce the "orgasmic platform," an area at the distal third of the vagina where blood becomes sequestered. Localized perivaginal swelling and vaginal lubrication make up the changes in this stage of sexual response. Subsequently, ballooning of the proximal portion of the vagina and elevation of the uterus occurs. In the male, vasodilation of the cavernosal arteries and closure of the venous channels that drain the penis produce an erection. The third stage of sexual response is orgasm, while the fourth stage is resolution. Interruption or absence of any of the stages of the sexual response cycle can result in sexual dysfunction. One study found that 35% of males and 42% of females reported some form of sexual dysfunction. Read et al, *J. Public Health Med.,* 19(4): 387–391 (1997).

While there are obvious differences in the sexual response between males and females, one common aspect of the sexual response is the erectile response. The erectile response in both males and females is the result of engorgement of the erectile tissues of the genitalia with blood which is caused by the relaxation of smooth muscles in the arteries serving the genitalia.

In both pre-menopausal and menopausal females, sexual dysfunction can include, for example, sexual pain disorders, sexual desire disorders, sexual arousal dysfunction, orgasmic dysfunction, dyspareunia, and vaginismus. Sexual dysfunction can be caused, for example, by pregnancy, menopause, cancer, pelvic surgery, chronic medical illness or medications.

In males, some pharmacological methods of treating sexual dysfunctions are available, however, such methods have not proven to be highly satisfactory or without potentially severe side-effects. Papaverine now widely used to treat impotence, is generally effective in cases where the dysfunction is psychogenic or neurogenic and where severe atherosclerosis is not involved. Injection of papaverine, a smooth muscle relaxant, or phenoxybenzamine, a non-specific antagonist and hypotensive, into corpus cavernosum has been found to cause an erection sufficient for vaginal penetration, however, these treatments are not without the serious and often painful side effect of priapism. Also, in cases where severe atherosclerosis is not a cause of the dysfunction, intracavernosal injection of phentolamine, an α-adrenergic antagonist, is used.

As an alternative or, in some cases an adjunct to phosphodiesterase inhibition or α-adrenergic blockade for the treatment of erectile dysfunction, prostaglandin $E_1$ ($PGE_1$) has been administered to the penis or by intracavernosal injection. Two products containing $PGE_1$ have been approved by the U.S. Food and Drug Administration for the treatment of erectile dysfunction by intracavernosal injection (CAVERJECT®, Pharmacia & Upjohn Company, Kalamazoo, Mich.) and intraurethral administration (MUSE®, Vivus Incorporated, Mountain View, Calif.). A major side effect frequently associated with intracorpral or transurethral delivered $PGE_1$ is penile pain and burning. In addition, priapism, infection, penile corporal fibrosis, fibrotic nodules, hypotension, bruising and hematomas may occur. Swelling and ulceration of the penile skin at the site of injection have also been reported.

There is a need in the art for the treatment of sexual dysfunctions, particularly treatments that do not have the undesirable side effects of those agents currently being used. The present invention is directed to these, as well as other, important ends.

SUMMARY OF THE INVENTION

Nitric oxide (NO) has been shown to mediate a number of actions including the bactericidal and tumoricidal actions of macrophages and blood vessel relaxation of endothelial cells. NO and NO donors have also been implicated as mediators of nonvascular smooth muscle relaxation. As described herein, this effect includes the dilation of the corpus cavernosum smooth muscle, an event involved in the sexual response process in both males and females. However, the effects of modified prostaglandins, which are directly or indirectly linked with a nitric oxide adduct, have not been previously investigated.

In the process of arriving at the present invention, it was unexpectedly discovered that the adverse effects associated with prostaglandins can be avoided by the use of nitrosated and/or nitrosylated prostaglandin compounds or by the use of a prostaglandin in combination with a S-nitrosothiol compound. Such adverse effects include hypotension, syncope, as well as priapism and pain. The smooth muscle relaxant properties of prostaglandins and of compounds that donate, release or transfer nitrogen monoxide or elevate levels of endogenous nitric oxide or endothelium-derived relaxing factor (EDRF) or is a substrate for nitric oxide synthase work together to permit the same efficacy with lower doses of the prostaglandins.

One embodiment of the present invention provides novel nitrosated and/or nitrosylated prostaglandins. The prostaglandins can be nitrosated and/or nitrosylated through one or more sites such as oxygen (hydroxyl condensation), sulfur (sulfhydryl condensation), carbon and/or nitrogen. The present invention also provides compositions comprising a therapeutically effective amount of such compounds in a pharmaceutically acceptable carrier.

Another embodiment of the present invention provides compositions comprising at least one nitrosated and/or nitrosylated prostaglandin, and at least one compound that donates, transfers or releases nitrogen monoxide as a charged species, i.e., nitrosonium ($NO^+$) or nitroxyl ($NO-$), or as the neutral species, nitric oxide (NO.), and/or stimulates endogenous production of nitric oxide or EDRF in vivo and/or is a substrate for nitric oxide synthase. The present invention also provides for such compositions in a pharmaceutically acceptable carrier.

Yet another embodiment of the present invention provides compositions comprising at least one nitrosated and/or nitrosylated prostaglandin and at least one vasoactive drug, and, optionally, at least one compound that donates, transfers or releases nitrogen monoxide as a charged species, i.e., nitrosonium ($NO^+$) or nitroxyl ($NO-$), or as the neutral species, nitric oxide (NO.), and/or stimulates endogenous production of nitric oxide or EDRF in vivo and/or is a substrate for nitric oxide synthase. The invention also provides for such compositions in a pharmaceutically acceptable carrier.

In another embodiment, the present invention provides pharmaceutical compositions comprising at least one prostaglandin and at least one S-nitrosothiol compound, and, optionally, at least one vasoactive drug. The prostaglandin is preferably a prostaglandin $E_1$ ($PGE_1$) compound, more preferably alprostadil. The S-nitrosothiol compound is a compound that is capable of donating, transferring or releasing nitric oxide. The S-nitrosothiol compound is preferably S-nitrosoglutathione. The compositions can comprise one or more pharmaceutically acceptable carriers. The compositions are preferably in a form that can be administered by intracavernosal injection, by transurethral application, or by topical application.

Yet another embodiment of the present invention provides methods for treating and/or preventing sexual dysfunctions and/or enhancing sexual responses in patients, including males and females, by administering to a patient in need thereof a therapeutically effective amount of at least one nitrosated and/or nitrosylated prostaglandin and, optionally, at least one compound that donates, transfers or releases nitric oxide as a charged species, i.e., nitrosonium ($NO^+$) or nitroxyl ($NO-$), or as the neutral species, nitric oxide (NO.), and/or stimulates endogenous production of nitric oxide or EDRF in vivo and/or is a substrate for nitric oxide synthase. The methods can further comprise administering a therapeutically effective amount of at least one vasoactive agent. Alternatively, the methods for treating and/or preventing sexual dysfunctions and/or enhancing sexual responses in patients, including males and females, can comprise administering a therapeutically effective amount of at least one nitrosated and/or nitrosylated prostaglandin, at least one vasoactive agent, and, optionally, at least one compound that donates, transfers or releases nitric oxide as a charged species, i.e., nitrosonium ($NO^+$) or nitroxyl ($NO-$), or as the neutral species, nitric oxide (NO.), and/or stimulates endogenous production of nitric oxide or EDRF in vivo and/or is a substrate for nitric oxide synthase. The nitrosated and/or nitrosylated prostaglandins, nitric oxide donors, and/or vasoactive agents can be administered separately or as components of the same composition in one or more pharmaceutically acceptable carriers.

Another embodiment of the present invention provides methods for preventing or treating sexual dysfunctions or enhancing sexual responses in patients, including males and females, by administering a therapeutically effective amount of at least one prostaglandin and at least one S-nitrosothiol compound, and, optionally, at least one vasoactive agent. Preferably, the prostaglandin is a prostaglandin $E_1$ ($PGE_1$) compound, more preferably alprostadil. The S-nitrosothiol compound is a compound that is capable of donating, transferring or releasing nitric oxide. Preferably, the S-nitrosothiol compound is S-nitrosoglutathione (GS—NO). In the methods of the present invention, the compounds can be administered separately or as components of the same composition. The compounds or compositions are preferably administered from about 1 minute to about 60 minutes prior to sexual activity or sexual intercourse, preferably about 2 minutes to about 20 minutes prior to sexual activity or sexual intercourse, more preferably about 5 minutes to about 10 minutes prior to sexual activity or sexual intercourse, to prevent or treat sexual dysfunctions or to enhance sexual responses in patients. The compounds or compositions of the invention are preferably administered by intracavernosal injection, by transurethral application or by topical application.

The present invention also describes methods to prevent and treat cerebrovascular disorders, cardiovascular disorders, benign prostatic hyperplasia (BPH), glaucoma, peptic ulcers and to induce abortions by administering to a patient in need thereof at least one prostaglandin and at least one S-nitrosothiol compound or by administering at least one nitrosated and/or nitrosylated prostaglandin and, optionally, at least one compound that donates, transfers or releases nitric oxide as a charged species or as a neutral species and/or stimulates endogenous production of nitric oxide or EDRF in vivo. These methods may further comprise administering at least one vasoactive agent.

These and other aspects of the present invention are described in detail below.

DETAILED DESCRIPTION OF THE INVENTION

Figure 1:
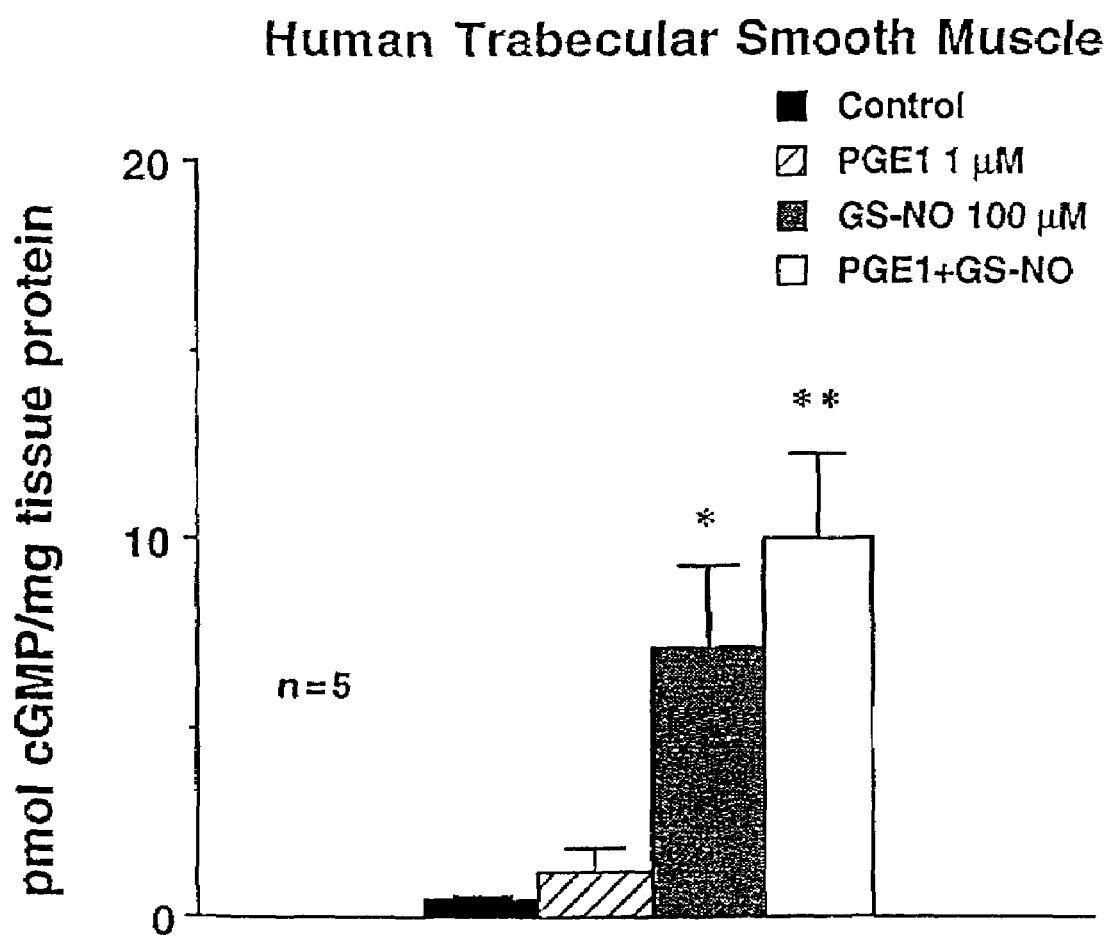
FIG. 1 is a measurement of cyclic GMP (cGMP) levels in trabecular smooth muscle expressed as picomole of cGMP per milligram of protein. The prepared tissues were incubated with (a) vehicle, control (filled bar); (b) 1 µM $PGE_1$ (hatched bar); (c) 100 µM GS—NO (shaded bar); and (d) combination of 1 µM $PGE_1$ and 100 µM GS—NO (open bar). The cGMP levels for 5 tissue samples were measured for each condition tested (n=5). * $P<0.05$, ** $P<0.01$ vs control using one way ANOVA analysis followed by Student-Newmann-Keuls post-hoc test using GraphPad InStat software for Apple computers.

As used throughout the disclosure, the following terms, unless otherwise indicated, shall be understood to have the following meanings.

"Patient" refers to animals, preferably mammals, more preferably humans.

"Transdermal" refers to the delivery of a compound by passage through the skin and into the blood stream.

"Transmucosal" refers to delivery of a compound by passage of the compound through the mucosal tissue and into the blood stream.

"Penetration enhancement" or "permeation enhancement" refers to an increase in the permeability of the skin or mucosal tissue to a selected pharmacologically active compound such that the rate at which the compound permeates through the skin or mucosal tissue is increased.

"Carriers" or "vehicles" refers to carrier materials suitable for compound administration and include any such material known in the art such as, for example, any liquid, gel, solvent, liquid diluent, solubilizer, or the like, which is non-toxic and which does not interact with any components of the composition in a deleterious manner.

"Nitric oxide adduct" or "NO adduct" refers to compounds and functional groups which, under physiological conditions, can donate, release and/or directly or indirectly transfer any of the three redox forms of nitrogen monoxide (NO$^+$, NO$^-$, NO.), such that the biological activity of the nitrogen monoxide species is expressed at the intended site of action.

"Nitric oxide releasing" or "nitric oxide donating" refers to methods of donating, releasing and/or directly or indirectly transferring any of the three redox forms of nitrogen monoxide (NO$^+$, NO−, NO.), such that the biological activity of the nitrogen monoxide species is expressed at the intended site of action.

"Nitric oxide donor" or "NO donor" refers to compounds that donate, release and/or directly or indirectly transfer a nitrogen monoxide species, and/or stimulate the endogenous production of nitric oxide or endothelium-derived relaxing factor (EDRF) in vivo and/or elevate endogenous levels of nitric oxide or EDRF in vivo. "NO donor" also includes compounds that are substrates for nitric oxide synthase.

"Alkyl" refers to a lower alkyl group, a haloalkyl group, an alkenyl group, an alkynyl group, a bridged cycloalkyl group, a cycloalkyl group or a heterocyclic ring, as defined herein.

"Lower alkyl" refers to branched or straight chain acyclic alkyl group comprising one to about ten carbon atoms (preferably one to about eight carbon atoms, more preferably one to about six carbon atoms). Exemplary lower alkyl groups include methyl, ethyl, n-propyl, isopropyl, n-butyl, isobutyl, sec-butyl, t-butyl, pentyl, neopentyl, iso-amyl, hexyl, octyl, and the like.

"Haloalkyl" refers to a lower alkyl group, an alkenyl group, an alkynyl group, a bridged cycloalkyl group, a cycloalkyl group or a heterocyclic ring, as defined herein, to which is appended one or more halogens, as defined herein. Exemplary haloalkyl groups include trifluoromethyl, chloromethyl, 2-bromobutyl, 1-bromo-2-chloro-pentyl, and the like.

"Alkenyl" refers to a branched or straight chain C$_2$–C$_{10}$ hydrocarbon (preferably a C$_2$–C$_8$ hydrocarbon, more preferably a C$_2$–C$_6$ hydrocarbon) which can comprise one or more carbon—carbon double bonds. Exemplary alkenyl groups include propylenyl, buten-1-yl, isobutenyl, penten-1-yl, 2,2-methylbuten-1-yl, 3-methylbuten-1-yl, hexan-1-yl, hepten-1-yl, octen-1-yl, and the like.

"Alkynyl" refers to an unsaturated acyclic C$_2$–C$_{10}$ hydrocarbon (preferably a C$_2$–C$_8$ hydrocarbon, more preferably a C$_2$–C$_6$ hydrocarbon) which can comprise one or more carbon—carbon triple bonds. Exemplary alkynyl groups include ethynyl, propynyl, butyn-1-yl, butyn-2-yl, pentyl-1-yl, pentyl-2-yl, 3-methylbutyn-1-yl, hexyl-1-yl, hexyl-2-yl, hexyl-3-yl, 3,3-dimethyl-butyn-1-yl, and the like.

"Bridged cycloalkyl" refers to two or more cycloalkyl groups, heterocyclic groups, or a combination thereof fused via adjacent or non-adjacent atoms. Bridged cycloalkyl groups can be unsubstituted or substituted with one, two or three substituents independently selected from alkyl, alkoxy, amino, alkylamino, dialkylamino, hydroxy, halo, carboxyl, alkylcarboxylic acid, aryl, amidyl, ester, alkylcarboxylic ester, carboxamido, alkylcarboxamido, oxo and nitro. Exemplary bridged cycloalkyl groups include adamantyl, decahydronapthyl, quinuclidyl, 2,6-dioxabicyclo[3.3.0]octane, 7-oxabycyclo[2.2.1]heptyl, 8-azabicyclo[3,2,1]oct-2-enyl and the like.

"Cycloalkyl" refers to a saturated or unsaturated cyclic hydrocarbon comprising from about 3 to about 8 carbon atoms. Cycloalkyl groups can be unsubstituted or substituted with one, two or three substituents independently selected from alkyl, alkoxy, amino, alkylamino, dialkylamino, arylamino, diarylamino, alkylarylamino, aryl, amidyl, ester, hydroxy, halo, carboxyl, alkylcarboxylic acid, alkylcarboxylic ester, carboxamido, alkylcarboxamido, oxo and nitro.

Exemplary cycloalkyl groups include cyclopropyl, cyclobutyl, cyclopentyl, cyclohexyl, cyclohexenyl, cyclohepta,1,3-dienyl, and the like.

"Heterocyclic ring or group" refers to a saturated, unsaturated, cyclic or aromatic or polycyclic hydrocarbon group having about 3 to about 12 carbon atoms (preferably about 4 to about 6 carbon atoms) where 1 to about 4 carbon atoms are replaced by one or more nitrogen, oxygen and/or sulfur atoms. Sulfur maybe in the thio, sulfinyl or sulfonyl oxidation state. The heterocyclic ring or group can be fused to an aromatic hydrocarbon group. Heterocyclic groups can be unsubstituted or substituted with one, two or three substituents independently selected from alkyl, alkoxy, amino, alkylamino, dialkylamino, arylamino, diarylamino, alkylarylamino, hydroxy, oxo, thial, halo, carboxyl, carboxylic ester, alkylcarboxylic acid, alkylcarboxylic ester, aryl, arylcarboxylic acid, arylcarboxylic ester, amidyl, ester, carboxamindo, alkylcarboxamido, arylcarboxamido, sulfonic acid, sulfonic ester, sulfonamido and nitro. Exemplary heterocyclic groups include pyrrolyl, 3-pyrrolinyl,4,5,6-trihydro-2H-pyranyl, pyridinyl, 1,4-dihydropyridinyl, pyrazolyl, triazolyl, pyrimidinyl, pyridazinyl, oxazolyl, thiazolyl, imidazolyl, indolyl, thiophenyl, furanyl, tetrhydrofuranyl, tetrazolyl, 2-pyrrolinyl, 3-pyrrolinyl, pyrrolindinyl, oxazolindinyl 1,3-dioxolanyl, 2,6-dioxabicyclo[3,3,0]octanyl, 2-imidazonlinyl, imidazolindinyl, 2-pyrazolinyl, pyrazolidinyl, isoxazolyl, isothiazolyl, 1,2,3-oxadiazolyl, 1,2,3-triazolyl, 1,3,4-thiadiazolyl, 2H-pyranyl, 4H-pyranyl, piperidinyl, 1,4-dioxanyl, morpholinyl, 1,4-dithianyl, thiomorpholinyl, pyrazinyl, piperazinyl, 1,3,5-triazinyl, 1,3,5-trithianyl, benzo(b)thiophenyl, benzimidazolyl, quinolinyl, and the like.

"Heterocyclic compounds" refer to mono- and polycyclic compounds comprising at least one aryl or heterocyclic ring.

"Aryl" refers to a monocyclic, bicyclic, carbocyclic or heterocyclic ring system comprising one or two aromatic rings. Exemplary aryl groups include phenyl, pyridyl, napthyl, quinoyl, tetrahydronaphthyl, furanyl, indanyl, indenyl, indoyl, and the like. Aryl groups (including bicylic aryl groups) can be unsubstituted or substituted with one, two or three substituents independently selected from alkyl, alkoxy, amino, alkylamino, dialkylamino, arylamino, diarylamino, alkylarylamino, hydroxy, carboxyl, carboxylic ester, alkylcarboxylic acid, alkylcarboxylic ester, aryl, arylcarboxylic acid, arylcarboxylic ester, alkylcarbonyl, arylcarbonyl, amidyl, ester, carboxamido, alkylcarboxamido, carbomyl, sulfonic acid, sulfonic ester, sulfonamido and nitro. Exemplary substituted aryl groups include tetrafluorophenyl, pentafluorophenyl, sulfonamide, alkylsulfonyl, arylsulfonyl, and the like.

"Alkylaryl" refers to an alkyl group, as defined herein, to which is appended an aryl group, as defined herein. Exemplary alkylaryl groups include benzyl, phenylethyl, hydroxybenzyl, fluorobenzyl, fluorophenylethyl, and the like.

"Arylalkyl" refers to an aryl radical, as defined herein, attached to an alkyl radical, as defined herein.

"Cycloalkylalkyl" refers to a cycloalkyl radical, as defined herein, attached to an alkyl radical, as defined herein.

"Heterocyclicalkyl" refers to a heterocyclic ring radical, as defined herein, attached to an alkyl radical, as defined herein.

"Cycloalkenyl" refers to an unsaturated cyclic hydrocarbon having about 3 to about 10 carbon atoms (preferably about 3 to about 8 carbon atoms, more preferably about 3 to about 6 carbon atoms) comprising one or more carbon—carbon double bonds.

"Arylheterocyclic ring" refers to a bi- or tricyclic ring comprised of an aryl ring, as defined herein, appended via two adjacent carbon atoms of the aryl ring to a heterocyclic ring, as defined herein. Exemplary arylheterocyclic rings include dihydroindole, 1,2,3,4-tetra-hydroquinoline, and the like.

"Alkoxy" refers to $R_{50}O$—, wherein $R_{50}$ is an alkyl group, as defined herein. Exemplary alkoxy groups include methoxy, ethoxy, t-butoxy, cyclopentyloxy, and the like.

"Arylalkoxy or alkoxyaryl" refers to an alkoxy group, as defined herein, to which is appended an aryl group, as defined herein. Exemplary arylalkoxy groups include benzyloxy, phenylethoxy, chlorophenylethoxy, and the like.

"Alkoxyalkyl" refers to an alkoxy group, as defined herein, appended to an alkyl group, as defined herein. Exemplary alkoxyalkyl groups include methoxymethyl, methoxyethyl, isopropoxymethyl, and the like.

"Alkoxyhaloalkyl" refers to an alkoxy group, as defined herein, appended to a haloalkyl group, as defined herein. Exemplary alkoxyhaloalkyl groups include 4-methoxy-2-chlorobutyl and the like.

"Cycloalkoxy" refers to $R_{54}O$—, wherein $R_{54}$ is a cycloalkyl group or a bridged cycloalkyl group, as defined herein. Exemplary cycloalkoxy groups include cyclopropyloxy, cyclopentyloxy, cyclohexyloxy, and the like.

"Haloalkoxy" refers to a haloalkyl group, as defined herein, to which is appended an alkoxy group, as defined herein. Exemplary haloalkyl groups include 1,1,1-trichloroethoxy, 2-bromobutoxy, and the like.

"Hydroxy" refers to —OH.

"Oxo" refers to =O.

"Oxy" refers to —O$^-$R$_{77}$$^+$ wherein $R_{77}$ is an organic or inorganic cation.

"Organic cation" refers to a positively charged organic ion. Exemplary organic cations include alkyl substituted ammonium cations, and the like.

"Inorganic cation" refers to a positively charged metal ion. Exemplary inorganic cations include Group I metal cations such as for example, sodium, potassium, and the like.

"Hydroxyalkyl" refers to a hydroxy group, as defined herein, appended to an alkyl group, as defined herein.

"Amino" refers to —NH$_2$.

"Nitrate" refers to —O—NO$_2$.

"Nitrite" refers to —O—NO.

"Thionitrate" refers to —S—NO$_2$.

"Thionitrite" and "nitrosothiol" refer to —S—NO.

"Nitro" refers to the group —NO$_2$ and "nitrosated" refers to compounds that have been substituted therewith.

"Nitroso" refers to the group —NO and "nitrosylated" refers to compounds that have been substituted therewith.

"Nitrile" and "cyano" refer to —CN.

"Halogen" or "halo" refers to iodine (I), bromine (Br), chlorine (Cl), and/or fluorine (F).

"Alkylamino" refers to $R_{50}NH$—, wherein $R_{50}$ is an alkyl group, as defined herein. Exemplary alkylamino groups include methylamino, ethylamino, butylamino, cyclohexylamino, and the like.

"Arylamino" refers to $R_{55}NH$—, wherein $R_{55}$ is an aryl group, as defined herein.

"Dialkylamino" refers to $R_{50}R_{52}N$—, wherein $R_{50}$ and $R_{52}$ are each independently an alkyl group, as defined herein. Exemplary dialkylamino groups include dimethylamino, diethylamino, methyl propargylamino, and the like.

"Diarylamino" refers to $R_{55}R_{60}N$—, wherein $R_{55}$ and $R_{60}$ are each independently an aryl group, as defined herein.

"Alkylarylamino" refers to $R_{50}R_{55}N$—, wherein $R_{50}$ is an alkyl group, as defined herein, and $R_{55}$ is an aryl group, as defined herein.

"Aminoalkyl" refers to an amino group, an alkylamino group, a dialkylamino group, an arylamino group, a diarylamino group, an alkylarylamino group or a heterocyclic ring, as defined herein, to which is appended an alkyl group, as defined herein.

"Aminoaryl" refers to an amino group, an alkylamino group, a dialkylamino group, an arylamino group, a diarylamino group, an alkylarylamino group or a heterocyclic ring, as defined herein, to which is appended an aryl group, as defined herein.

"Thio" refers to —S—.

"Sulfinyl" refers to —S(O)—.

"Methanthial" refers to —C(S)—.

"Thial" refers to =S.

"Sulfonyl" refers to —S(O)$_2^-$.

"Sulfonic acid" refers to —S(O)$_2$OR$_{76}$, wherein $R_{76}$ is a hydrogen, an organic cation or an inorganic cation.

"Alkylsulfonic acid" refers to a sulfonic acid group, as defined herein, appended to an alkyl group, as defined herein.

"Arylsulfonic acid" refers to an sulfonic acid group, as defined herein, appended to an aryl group, as defined herein "Sulfonic ester" refers to —S(O)$_2$OR$_{58}$' wherein $R_{58}$ is an alkyl group, an aryl group, an alkylaryl group or an aryl heterocyclic ring, as defined herein.

"Sulfonamido" refers to —S(O)$_2$—N(R$_{51}$)(R$_{57}$), wherein $R_{51}$ and $R_{57}$ are each independently a hydrogen atom, an alkyl group, an aryl group, an alkylaryl group, or an arylheterocyclic ring, as defined herein, and $R_{51}$ and $R_{57}$ when taken together are a heterocyclic ring, a cycloalkyl group or a bridged cycloalkyl group, as defined herein.

"Alkylsulfonamido" refers to a sulfonamido group, as defined herein, appended to an alkyl group, as defined herein.

"Arylsulfonamido" refers to a sulfonamido group, as defined herein, appended to an aryl group, as defined herein.

"Alkylthio" refers to $R_{50}S$—, wherein $R_{50}$ is an alkyl group, as defined herein.

"Arylthio" refers to $R_{55}S$—, wherein $R_{55}$ is an aryl group, as defined herein.

"Cycloalkylthio" refers to $R_{54}S$—, wherein $R_{54}$ is a cycloalkyl group or a bridged cycloalkyl group, as defined herein. Exemplary cycloalkylthio groups include cyclopropylthio, cyclopentylthio, cyclohexylthio, and the like.

"Alkylsulfinyl" refers to $R_{50}$—S(O)—, wherein $R_{50}$ is an alkyl group, as defined herein.

"Alkylsulfonyl" refers to $R_{50}$—S(O)$_2$—, wherein $R_{50}$ is an alkyl group, as defined herein.

"Arylsulfinyl" refers to $R_{55}$—S(O)—, wherein $R_{55}$ is an aryl group, as defined herein.

"Arylsulfonyl" refers to $R_{55}$—S(O)$_2$—, wherein $R_{55}$ is an aryl group, as defined herein.

"Amidyl" refers to $R_{51}$C(O)N(R$_{57}$)— wherein $R_{51}$ and $R_{57}$ are each independently a hydrogen atom, an alkyl group, an aryl group, an alkylaryl group, or an arylheterocyclic ring, as defined herein.

"Ester" refers to $R_{51}$C(O)O— wherein $R_{51}$ is a hydrogen atom, an alkyl group, an aryl group, an alkylaryl group, or an arylheterocyclic ring, as defined herein.

"Carbamoyl" refers to —O—C(O)N(R$_{51}$)(R$_{57}$), wherein $R_{51}$ and $R_{57}$ are each independently a hydrogen atom, an alkyl group, an aryl group, an alkylaryl group or an aryl-heterocyclic ring, as defined herein, or $R_{51}$ and $R_{57}$ taken together are a heterocyclic ring, a cycloalkyl group or a bridged cycloalkyl group, as defined herein.

"Carbamate" refers to $R_{51}$O—C(O)N(R$_{57}$), wherein $R_{51}$ and $R_{57}$ are each independently a hydrogen atom, an alkyl group, an aryl group, an alkylaryl group or an arylheterocyclic ring, as defined herein, or $R_{51}$ and $R_{57}$ taken together are a heterocyclic ring, a cycloalkyl group or a bridged cycloalkyl group, as defined herein.

"Carboxyl" refers to —C(O)OR$_{76}$, wherein $R_{76}$ is a hydrogen, an organic cation or an inorganic cation, as defined herein.

"Carbonyl" refers to —C(O)—.

"Alkylcarbonyl" or "alkanoyl" refers to $R_{50}$—C(O)—, wherein $R_{50}$ is an alkyl group, as defined herein.

"Arylcarbonyl" or "aroyl" refers to $R_{55}$—C(O)—, wherein $R_{55}$ is an aryl group, as defined herein.

"Carboxylic ester" refers to —C(O)OR$_{58}$, wherein $R_{58}$ is an alkyl group, an aryl group, an alkylaryl group or an aryl heterocyclic ring, as defined herein.

"Alkylcarboxylic acid" and "alkylcarboxyl" refer to an alkyl group, as defined herein, appended to a carboxyl group, as defined herein.

"Alkylcarboxylic ester" refers to an alkyl group, as defined herein, appended to a carboxylic ester group, as defined herein.

"Arylcarboxylic acid" refers to an aryl group, as defined herein, appended to a carboxyl group, as defined herein.

"Arylcarboxylic ester" and "arylcarboxyl" refer to an aryl group, as defined herein, appended to a carboxylic ester group, as defined herein.

"Carboxamido" refers to —C(O)N(R$_{51}$)(R$_{57}$), wherein $R_{51}$ and $R_{57}$ are each independently a hydrogen atom, an alkyl group, an aryl group, an alkylaryl group or an aryl-heterocyclic ring, as defined herein, and $R_{51}$ and $R_{57}$ when taken together with the nitrogen to which they are attached form a heterocyclic ring, a cycloalkyl group or a bridged cycloalkyl group, as defined herein.

"Alkylcarboxamido" refers to an alkyl group, as defined herein, appended to a carboxamido group, as defined herein.

"Arylcarboxamido" refers to an aryl group, as defined herein, appended to a carboxamido group, as defined herein.

"Urea" refers to —N(R$_{59}$)—C(O)N(R$_{51}$)(R$_{57}$) wherein $R_{51}$, $R_{57}$, and $R_{59}$ are each independently a hydrogen atom, an alkyl group, an aryl group, an alkylaryl group, or an arylheterocyclic ring, as defined herein, or $R_{51}$ and $R_{57}$ taken together with the nitrogen to which they are attached form a heterocyclic ring, as defined herein.

"Phosphoryl" refers to —P(R$_{70}$)(R$_{71}$)(R$_{72}$), wherein $R_{70}$ is a lone pair of electrons, sulfur or oxygen, and $R_{71}$ and $R_{72}$ are each independently a covalent bond, a hydrogen, a lower alkyl, an alkoxy, an alkylamino, a hydroxy or an aryl, as defined herein.

The term "sexual dysfunction" generally includes any sexual dysfunction in a patient, including an animal, preferably a mammal, more preferably a human. The patient can be male or female. Sexual dysfunctions can include, for example, sexual desire disorders, sexual arousal disorders, orgasmic disorders and sexual pain disorders. Female sexual dysfunction refers to any female sexual dysfunction including, for example, sexual desire disorders, sexual arousal dysfunctions, orgasmic dysfunctions, sexual pain disorders, dyspareunia, and vaginismus. The female can be pre-menopausal or menopausal. Male sexual dysfunction refers to any male sexual dysfunctions including, for example, male erectile dysfunction and impotence.

The present invention is directed to the treatment and/or prevention of sexual dysfunctions in patients, including males and females, by administering the compounds and compositions described herein. The present invention is also directed to improving and/or enhancing sexual responses in patients, including males and females, by administering the compounds and/or compositions described herein. The novel compounds and novel compositions of the present invention are described in more detail herein.

Contemplated prostaglandins for use in the present invention include, for example, naturally occurring prostaglandins such as, for example, $PGE_0$, $PGE_1$, $PGA_1$, $PGB_1$, $PGF_1$, $PGF_2$, $PGE_{1\alpha}$, 19-hydroxy-$PGA_1$, 19-hydroxy-$PGB_1$, $PGE_2$, $PGA_2$, $PGB_2$, 19-hydroxy-$PGA_2$, 19-hydroxy-$PGB_2$, $PGE_3$, $PGF_3$, $PGD_2$, $PGI_2$, prostacyclins, thromboxanes, leukotrienes, 6-keto-$PGE_1$ derivatives and carbacyclin derivatives; or semisynthetic or synthetic derivatives of natural prostaglandins, including, but not limited to, carboprost tromethamine, dinoprost tromethamine, dinoprostone, gemeprost, metenoprost, sulprostone and triprost. Also included are the hydroxy derivatives of $PGE_2$ including, for example, 19-OH-$PGE_2$, 18-OH-$PGE_2$, 20-OH-$PGE_2$ and the salts and esters thereof as disclosed in WO 99/02164, the disclosure of which is incorporated by reference herein in its entirety. Other prostaglandin compound for use in the present invention include isoprostanes, such as 8-iso-$PGE_{2\alpha}$, 8-iso-$PGE_2$, $iPF_2\alpha$-VI, 12-iso-$PGF_{2\alpha}$, and the like, as described by, for example, Rokach et al *Prostaglandins*, 54: 823–851, (1997) and Rokach et al, *Prostaglandins*, 54: 853–873, (1997), the disclosure of which is incorporated by reference herein in its entirety.

Arbaprostil, alprostadil, beraprost, carboprost, cloprostenol, dimoxaprost, enprostil, enisoprost, fluprostenol, fenprostalene, gemeprost, latanoprost, limaprost, meteneprost, mexiprostil, misoprostol, misoprost, misoprostol acid, nocloprost, ornoprostil, prostalene, $PGE_1$, $PGE_2$, $PGF_1$, $PGF_{2\alpha}$, rioprostil, rosaprostol, remiprostol, sulprostone, trimoprostil, tiprostanide, unoprostone, viprostol, are the preferred prostaglandins and $PGE_1$ is the most preferred. $PGE_1$ compounds include, but are not limited to, alprostadil, misoprostol and enprostil and their α-cyclodextrin complexes. All the prostaglandins described herein can be nitrosated and/or nitrosylated following the methods described herein.

Sources of information for the above compounds include Goodman and Gilman, The Pharmacological Basis of Therapeutics (9th Ed.), McGraw-Hill, Inc. (1996), The Physician's Desk Reference (49th Ed.), Medical Economics (1995), Drug Facts and Comparisons (1993 Ed), Facts and Comparisons (1993), Merck Index on CD-ROM, Twelfth Edition, Version 12:1, (1996), STN Express, file phar and file registry, the disclosures of each of which are incorporated herein by reference in their entirety.

A principal aspect of the present invention relates to novel nitrosated and/or nitrosylated prostaglandins having formula (I):

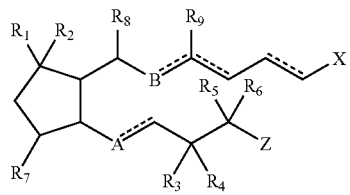

(I)

wherein the dotted lines indicate a single or a double bond;
$R_1$ is —$OD_1$ or —Cl;
$R_2$ and $R_8$ are a hydrogen; or $R_1$ and $R_2$ taken together are =$CH_2$ or =O;
$R_3$ and $R_4$ are each independently a hydrogen, —$OD_1$ or —$CH_3$;
$R_5$ and $R_6$ are each independently a hydrogen, —$OD_1$, —$CH_3$, —$OCH_3$ or —$CH$=$CH_2$;
$R_7$ is a hydrogen or —$OD_1$;
$R_9$ is hydrogen or absent when the carbon to which it is attached is the central carbon of an allene functionality; or $R_8$ and $R_9$ taken together with the chain to which they are attached form a substituted benzene ring with the proviso that $R_1$ is an oxygen atom which is attached to the carbon atom at the position of the benzene ring defined by B;
A is —CH=, —$CH_2$, —S—, or —O—;
B is —CH=, —$CH_2$, —S—, or —C(O)—;
X is —$CH_2OR_{11}$, —$C(O)OR_{11}$ or —$C(O)N(D_1)R_{12}$;
$R_{11}$ is $D_1$, a lower alkyl group, or

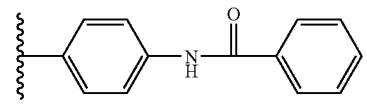

$R_{12}$ is —$S(O)_2CH_3$ or —$C(O)CH_3$;
Z is (a) an ethyl, (b) a butyl, (c) a hexyl, (d) a benzyl,

(e)

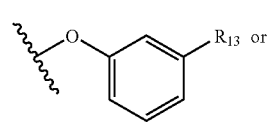

(f)

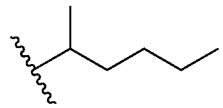

(g)

(h)

$R_{13}$ is a hydrogen or —Cl;
$D_1$ is a hydrogen or D; with the proviso that at least one $D_1$ in formula (I) must be D;
D is Q or K;
Q is —NO or —$NO_2$;
K is —$W_a$—$E_b$—$(C(R_e)(R_f))_p$—E—$(C(R_e)(R_f))_x$—$W_d$—$C(R_e)(R_f))_y$—$W_i$—$E_i$—$W_g$—$(C(R_e)(R_f))_z$—T—Q; with the proviso that when X is —$C(O)OD_1$ and $D_1$ is K, then K is not an alkyl, branched alkyl or cycloalkyl mononitrate; a benzoic acid substituted benzyloxy mononitrate; an ethylene glycol mononitrate; a polyethylene glycol mononitrate; the regioisomeric esters of glycerol dinitrate and oligomers thereof as disclosed in WO 98/58910;
a, b, c, d, g, i and j are each independently an integer from 0 to 3;
p, x, y and z are each independently an integer from 0 to 10;

W at each occurrence is independently —C(O)—, —C(S)—, —T—, —(C($R_e$)($R_f$))$_h$—, an alkyl group, an aryl group, a heterocyclic ring, an arylheterocyclic ring, or —(CH$_2$CH$_2$O)$_q$—;

E at each occurrence is independently —T—, an alkyl group, an aryl group, —(C($R_e$)($R_f$))$_h$—, a heterocyclic ring, an arylheterocyclic ring, or —(CH$_2$CH$_2$O)$_q$—;

h is an integer form 1 to 10;

q is an integer from 1 to 5;

$R_e$ and $R_f$ are each independently a hydrogen, an alkyl, a cycloalkoxy, a halogen, a hydroxy, an hydroxyalkyl, an alkoxyalkyl, an arylheterocyclic ring, an alkylaryl, a cycloalkylalkyl, a heterocyclicalkyl, an alkoxy, a haloalkoxy, an amino, an alkylamino, a dialkylamino, an arylamino, a diarylamino, an alkylarylamino, an alkoxyhaloalkyl, a haloalkoxy, a sulfonic acid, a sulfonic ester, an alkylsulfonic acid, an arylsulfonic acid, an arylalkoxy, an alkylthio, an arylthio, a cycloalkylthio, a cycloalkenyl, a cyano, an aminoalkyl, an aminoaryl, an aryl, an arylalkyl, an alkylaryl, a carboxamido, a alkylcarboxamido, an arylcarboxamido, an amidyl, a carboxyl, a carbamoyl, a carbamate, an alkylcarboxylic acid, an arylcarboxylic acid, an alkylcarbonyl, an arylcarbonyl, an ester, a carboxylic ester, an alkylcarboxylic ester, an arylcarboxylic ester, a haloalkoxy, a sulfonamido, an alkylsulfonamido, an arylsulfonamido, a sulfonic ester, a urea, a phosphoryl, a nitro, —T—Q, or $R_e$ and $R_f$ are —(C($R_e$)($R_f$))$_k$—T—Q, (wherein $R_e$ and $R_f$ are as defined herein, or $R_e$ and $R_f$ taken together with the carbons to which they are attached form a carbonyl, a methanthial, a heterocyclic ring, a cycloalkyl group or a bridged cycloalkyl group;

k is an integer from 1 to 3;

T at each occurrence is independently a covalent bond, a carbonyl, an oxygen, —S(O)$_o$— or —N($R_a$)$R_i$—;

o is an integer from 0 to 2;

$R_a$ is a lone pair of electrons, a hydrogen or an alkyl group;

$R_i$ is a hydrogen, an alkyl, an aryl, an alkylcarboxylic acid, an arylcarboxylic acid, an alkylcarboxylic ester, an arylcarboxylic ester, an alkylcarboxamido, an arylcarboxamido, an alkylaryl, an alkylsulfinyl, an alkylsulfonyl, an arylsulfinyl, an arylsulfonyl, a sulfonamido, a carboxamido, a carboxylic ester, an amino alkyl, an amino aryl, —CH$_2$—C(T—Q)($R_e$)($R_f$), or —(N$_2$O$_2$—).M$^+$, wherein M+is an organic or inorganic cation; with the proviso that when $R_i$ is —CH$_2$—C(T—Q)($R_e$)($R_f$) or —(N$_2$O$_2$)$^-$.M$^+$, or $R_e$ or $R_f$ are T—Q or $R_e$ and $R_f$ are —(C($R_e$)($R_f$))$_k$—T—Q, wherein $R_e$ and $R_f$ are as defined herein, then the "—T—Q" subgroup can be a hydrogen, an alkyl, an alkoxy, an alkoxyalkyl, an aminoalkyl, a hydroxy, a heterocyclic ring or an aryl group;

In cases where $R_e$ and $R_f$ are a heterocyclic ring or $R_e$ and $R_f$ taken together with the carbon atoms to which they are attached are a heterocyclic ring, then $R_i$ can be a substituent on any disubstituted nitrogen contained within the radical where $R_i$ is as defined herein.

In cases where multiple designations of variables which reside in sequence are chosen as a "covalent bond" or the integer chosen is 0, the intent is to denote a single covalent bond connecting one radical to another. For example, $E_0$ would denote a covalent bond, while $E_2$ denotes (E—E) and (C($R_e$)($R_f$))$_2$ denotes —C($R_e$)($R_f$)—C($R_e$)($R_f$)—.

Compounds of the present invention which have one or more asymmetric carbon atoms may exist as the optically pure enantiomers, pure diastereomers, mixtures of enantiomers, mixtures of diastereomers, racemic mixtures of enantiomers, diastereomeric racemates or mixtures of diastereomeric racemates. It is to be understood that the present invention anticipates and includes within its scope all such isomers and mixtures thereof.

Another aspect of the present invention provides processes for making the novel compounds of the invention and to the intermediates useful in such processes. The compounds of the present invention of formula (I) can be synthesized by one skilled in the art following the methods and examples described herein. The reactions are performed in solvents appropriate to the reagents and materials used are suitable for the transformations being effected. It is understood by one skilled in the art of organic synthesis that the functionality present in the molecule must be consistent with the chemical transformation proposed. This will, on occasion, necessitate judgment by the routineer as to the order of synthetic steps, protecting groups required, and deprotection conditions. Substituents on the starting materials may be incompatible with some of the reaction conditions required in some of the methods described, but alternative methods and substituents compatible with the reaction conditions will be readily apparent to one skilled in the art. The use of sulfur, oxygen and nitrogen protecting groups is well known in the art for protecting thiol, alcohol, and amino groups against undesirable reactions during a synthetic procedure and many such protecting groups are known and described by, for example, Greene and Wuts, *Protective Groups in Organic Synthesis*, Third Edition, John Wiley & Sons, New York (1999).

Nitroso compounds of formula (I), where $R_1$, $R_2$, $R_3$, $R_4$, $R_5$, $R_6$, $R_7$, $R_8$, $R_9$, A, B, Z, $R_e$, $R_f$, and p are as defined herein, P$^1$ is an oxygen protecting group, and a nitrite containing carboxylic ester is representative of the X group as defined herein can be prepared as shown in Scheme 1. The acid of the compound of formula 1 is converted into the ester of the formula 2 by reaction with an appropriate monoprotected diol. Preferred methods for the preparation of esters are forming the mixed anhydride via reaction of the acid with a chloroformate, such as isobutylchloroformate, in the presence of a non-nucleophilic base, such as triethylamine, in an anhydrous inert solvent, such as dichloromethane, diethylether or THF. The mixed anhydride is then reacted with the monoprotected alcohol, preferably in the presence of a condensation catalyst, such as 4-dimethylamino pyridine (DMAP). Alternatively, the acid may first be converted to the acid chloride by treatment with oxalyl chloride in the presence of a catalytic amount of DMF. The acid chloride is then reacted with the monoprotected alcohol, preferably in the presence of a condensation catalyst, such as DMAP, and a tertiary amine base, such as triethyl amine, to produce the ester. Alternatively, the acid and monoprotected diol may be coupled to produce the ester by treatment with a dehydration agent, such as dicyclohexylcarbodiimide (DCC) or 1-(3 dimethylaminopropyl)-3-ethylcarbodiimide hydrochloride (EDAC.HCl) with or without a condensation catalyst, such as DMAP or 1-hydroxybenzotriazole (HOBt). Alternatively, the acid may first be converted into an alkali metal salt, such as the sodium, potassium or lithium salt, and reacted with an alkyl halide that also contains a protected hydroxyl group in a polar solvent, such as DMF, to produce the ester. Preferred protecting groups for the alcohol moiety are silyl ethers, such as a trimethylsilyl or a tert-butyldimethylsilyl ether. Deprotection of the hydroxyl moiety in the compound of formula 2 (fluoride ion is the preferred method for removing silyl ether protecting groups) followed by reaction with a suitable nitrosylating agent, such as thionyl chloride nitrite, thionyl dinitrite or nitrosonium tetrafluoroborate, in a suitable anhydrous solvent, such as dichlormethane, THF, DMF or acetonitrile, with or without an amine base, such as pyridine or triethylamine, produces the compound of formula IA.

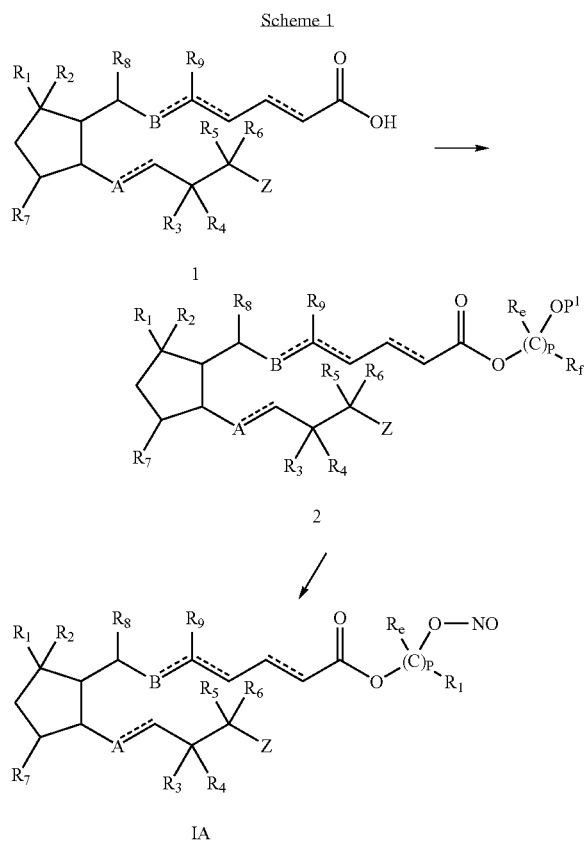

Nitroso compounds of formula (I), where $R_1$, $R_2$, $R_3$, $R_4$, $R_5$, $R_6$, $R_7$, $R_8$, $R_9$, A, B, Z, $R_e$, $R_f$, and p are as defined herein, $P^2$ is a sulfur protecting group, and a thionitrite containing carboxylic ester is representative of the X group as defined herein can be prepared as shown in Scheme 2. The appropriate acid of the compound of formula 1 is converted into the ester of the formula 3 by reaction with an appropriate protected thiol containing alcohol. Preferred methods for the preparation of esters are initially forming the mixed anhydride via reaction of the acid with a chloroformate, such as isobutylchloroformate, in the presence of a non-nucelophilic base, such as triethylamine, in an anhydrous inert solvent, such as diethylether or THF. The mixed anhydride is then reacted with the protected thiol-containing alcohol, preferably in the presence of a condensation catalyst, such as DMAP. Alternatively, the acid may first be converted to the acid chloride by treatment with oxalyl chloride in the presence of a catalytic amount of DMF. The acid chloride is then reacted with the protected thiol containing alcohol, preferably in the presence of a condensation catalyst, such as DMAP, and a tertiary amine base, such as triethyl amine, to produce an ester. Alternatively, the appropriate acid and protected thiol-containing alcohol may be coupled to produce the ester by treatment with a dehydration agent, such as DCC or EDAC.HCl, with or without a condensation catalyst, such as DMAP or HOBt. Alternatively, the acid may first be converted into an alkali metal salt, such as the sodium, potassium or lithium salt, which is then reacted with an alkyl halide which also contains a protected thiol group in a polar solvent, such as DMF, to produce the ester. Preferred protecting groups for the thiol moiety are as a thioester, such as thioacetate or thiobenzoate, as a disulfide, as a thiocarbamate, such as N-methoxymethyl thiocarbamate, or as a thioether, such as paramethoxybenzyl thioether, a 2,4,6-trimethoxybenzyl thioether, a tetrahydropyranyl thioether, or a S-triphenylmethyl thioether. Deprotection of the thiol moiety in the compound of formula 3 (zinc in dilute aqueous acid, triphenylphosphine in water and sodium borohydride are preferred methods for reducing disulfide groups, aqueous base or sodium methoxide in methanol is typically used to hydrolyze thioesters, aqueous base removes N-methoxymethyl thiocarbamates and mercuric trifluoroacetate, silver nitrate or strong acids such as trifluoroacetic or hydrochloric acid and heat are used to remove a paramethoxybenzyl thioether, 2,4,6-trimethoxybenzyl thioether, a tetrahydropyranyl thioether or a S-triphenylmethyl thioether group) followed by reaction with a suitable nitrosylating agent, such as thionyl chloride nitrite, thionyl dinitrite, a lower alkyl nitrite, such as tert-butyl nitrite, or nitrosium tetrafluoroborate, in a suitable anhydrous solvent, such as methylene chloride, THF, DMF or acetonitrile, with or without an amine base, such as pyridine or triethylamine, produces the compound of formula IB. Alternatively, treatment of the deprotected thiol with a stoichiometric quantity of sodium nitrite in aqueous acid produces the compound of formula IB.

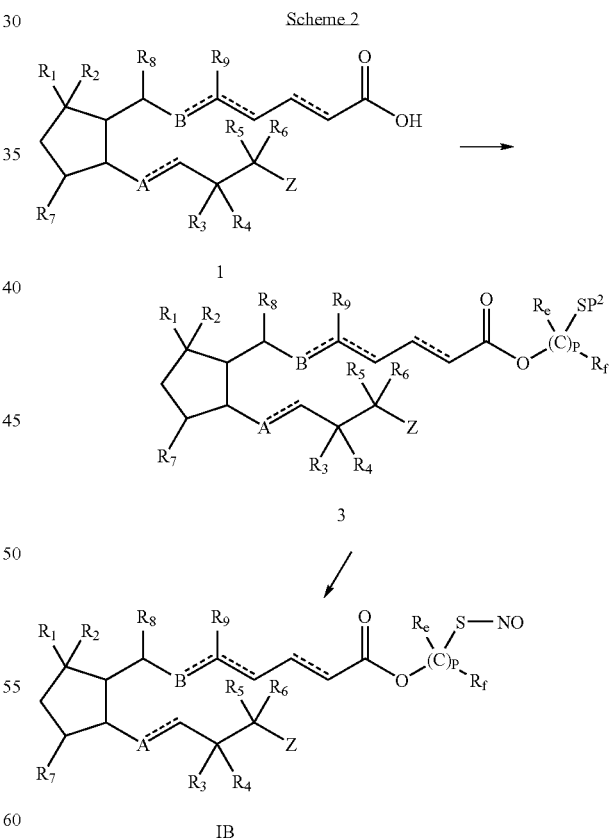

Nitroso compounds of formula (I), where $R_1$, $R_2$, $R_3$, $R_4$, $R_5$, $R_6$, $R_7$, $R_8$, $R_9$, A, B, Z, $R_e$, $R_f$ and p are as defined herein, and a nitrate containing carboxylic ester is representative of the X group as defined herein can be prepared as shown in Scheme 3. The appropriate acid of the compound of formula 1 is converted into the ester of the formula IC by reaction with an appropriate nitrate containing alcohol. Preferred methods for the preparation of esters are initially forming the mixed anhydride via reaction of the acid with a chloroformate, such as isobutylchloroformate, in the presence of a non-nucelophilic base, such as triethylamine, in an anhydrous inert solvent, such as diethylether or THF. The mixed anhydride is then reacted with the nitrate containing alcohol, preferably in the presence of a condensation catalyst, such as DMAP. Alternatively, the acid may first be converted to the acid chloride by treatment with oxalyl chloride in the presence of a catalytic amount of DMF. The acid chloride is then reacted with the protected thiol containing alcohol, preferably in the presence of a condensation catalyst, such as DMAP, and a tertiary amine base, such as triethyl amine, to produce an ester. Alternatively, the appropriate acid and protected thiol-containing alcohol may be coupled to produce the ester by treatment with a dehydration agent, such as DCC or EDAC.HCl with or without a condensation catalyst, such as DMAP or HOBt.

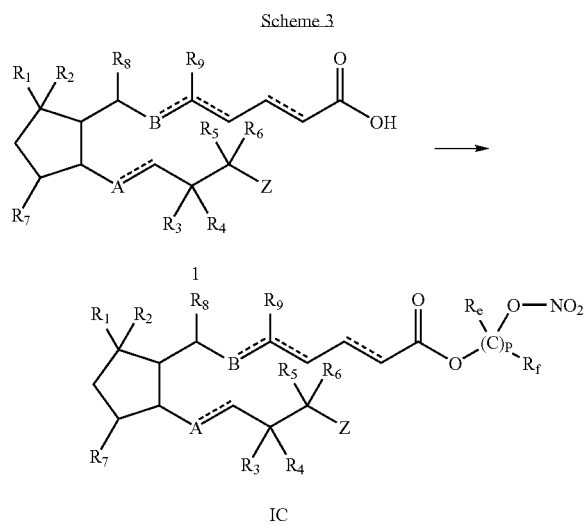

The compounds of the present invention include prostaglandins, such as those described herein, which have been nitrosated and/or nitrosylated through one or more sites such as oxygen (hydroxyl condensation), sulfur (sulfhydryl condensation), carbon and/or nitrogen. The nitrosated and/or nitrosylated prostaglandins of the present invention are capable of donating, transfering and/or releasing a biologically active form of nitrogen monoxide (i.e., nitric oxide).

Nitrogen monoxide can exist in three forms: NO– (nitroxyl), NO. (uncharged nitric oxide) and NO$^+$ (nitrosonium). NO. is a highly reactive short-lived species that is potentially toxic to cells. This is critical because the pharmacological efficacy of NO depends upon the form in which it is delivered. In contrast to the nitric oxide radical (NO.), nitrosonium (NO$^+$) does not react with $O_2$ or $O_2^-$ species, and functionalities capable of transferring and/or releasing NO$^+$ and NO– are also resistant to decomposition in the presence of many redox metals. Consequently, administration of charged NO equivalents (positive and/or negative) is a more effective means of delivering a biologically active NO to the desired site of action.

Compounds contemplated for use in the present invention (e.g., prostaglandins substituted with one or more NO and/or $NO_2$ groups) can be used in combination with nitric oxide and compounds that release nitric oxide (i.e., compounds that release nitric oxide or otherwise directly or indirectly deliver or transfer nitric oxide to a site of its activity, such as on a cell membrane, and/or elevate or stimulate production of endogenous nitric oxide or EDRF in vivo and/or is a substrate for nitric oxide synthase). "In combination" as used herein can mean that (i) the nitrosated and/or nitrosylated prostaglandin and nitric oxide donor can be present together in the same composition; (ii) the nitrosated and/or nitrosylated prostaglandin and nitric oxide donor can be administered separately; and/or (iii) the nitrosated and/or nitrosylated prostaglandin and nitric oxide donor can be together in the form of a kit.

The term "nitric oxide" encompasses uncharged nitric oxide (NO.) and charged nitrogen monoxide species, preferably charged nitrogen monoxide species, such as nitrosonium ion (NO$^-$) and nitroxyl ion (NO–). The reactive form of nitric oxide can be provided by gaseous nitric oxide. The nitrogen monoxide releasing, delivering or transferring compounds include any and all such compounds which provide nitrogen monoxide to its intended site of action in a form active for its intended purpose. The term "NO adducts" encompasses any nitrogen monoxide releasing, delivering or transferring compounds, including, for example, S nitrosothiols, nitrites, nitrates, S-nitrothiols, sydnonimines, 2-hydroxy-2-nitrosohydrazines (NONOates), (E)-alkyl-2-[(E)-hydroxyimino]-5-nitro-3-hexene amines or amides, nitrosoamines, furoxans as well as substrates for the endogenous enzymes which synthesize nitric oxide. The "NO adducts" can be mono-nitrosylated, poly-nitrosylated, mono-nitrosated and/or poly-nitrosated or a combination thereof at a variety of naturally susceptible or artificially provided binding sites for biologically active forms of nitrogen monoxide.

One group of NO adducts is the S-nitrosothiols, which are compounds that include at least one —S—NO group. These compounds include S-nitroso-polypeptides (the term "polypeptide" includes proteins and polyamino acids that do not possess an ascertained biological function, and derivatives thereof); S-nitrosylated amino acids (including natural and synthetic amino acids and their stereoisomers and racemic mixtures and derivatives thereof); S-nitrosylated sugars; S-nitrosylated, modified and unmodified, oligonucleotides (preferably of at least 5, and more preferably 5–200 nucleotides); straight or branched, saturated or unsaturated, aliphatic or aromatic, substituted or unsubstituted S-nitrosylated hydrocarbons; and S-nitroso heterocyclic compounds. S-nitrosothiols and methods for preparing them are described in U.S. Pat. Nos. 5,380,758 and 5,703,073; WO 97/27749; WO 98/19672; and Oae et al, Org. Prep. Proc. Int., 15(3):165–198 (1983), the disclosures of each of which are incorporated by reference herein in their entirety.

Another embodiment of the present invention is S-nitroso amino acids where the nitroso group is linked to a sulfur group of a sulfur-containing amino acid or derivative thereof. Such compounds include, for example, S-nitroso-N-acetylcysteine, S-nitroso-captopril, S-nitroso-N-acetyl-penicillamine, S-nitroso-homocysteine, S-nitroso-cysteine and S-nitroso-glutathione.

Suitable S-nitrosylated proteins include thiol-containing proteins (where the NO group is attached to one or more sulfur groups on an amino acid or amino acid derivative thereof) from various functional classes including enzymes, such as tissue-type plasminogen activator (TPA) and cathepsin B; transport proteins, such as lipoproteins; heme proteins, such as hemoglobin and serum albumin; and biologically protective proteins, such as immunoglobulins, antibodies and cytokines. Such nitrosylated proteins are described in WO 93/09806, the disclosure of which is incorporated by reference herein in its entirety. Examples include polynitrosylated albumin where one or more thiol or other nucleophilic centers in the protein are modified.

Other examples of suitable S-nitrosothiols include:
(i) $HS(C(R_e)(R_f))_mSNO$;
(ii) $ONS(C(R_e)(R_f))_mR_e$; and
(iii) $H_2N$—$CH(CO_2H)$—$(CH_2)_m$—$C(O)NH$—$CH(CH_2SNO)$—$C(O)NH$—$CH_2$—$CO_2H$;

wherein m is an integer from 2 to 20; $R_e$ and $R_f$ are each independently a hydrogen, an alkyl, a cycloalkoxy, a halogen, a hydroxy, an hydroxyalkyl, an alkoxyalkyl, an arylheterocyclic ring, an alkylaryl, a cycloalkylalkyl, a heterocyclicalkyl, an alkoxy, a haloalkoxy, an amino, an alkylamino, a dialkylamino, an arylamino, a diarylamino, an alkylarylamino, an alkoxyhaloalkyl, a haloalkoxy, a sulfonic acid, a sulfonic ester, an alkylsulfonic acid, an arylsulfonic acid, an arylalkoxy, an alkylthio, an arylthio, a cycloalkylthio, a cycloalkenyl, a cyano, an aminoalkyl, an aminoaryl, an aryl, an arylalkyl, an alkylaryl, a carboxamido, a alkylcarboxamido, an arylcarboxamido, an amidyl, a carboxyl, a carbamoyl, a carbamate, an alkylcarboxylic acid, an arylcarboxylic acid, an alkylcarbonyl, an arylcarbonyl, an ester, a carboxylic ester, an alkylcarboxylic ester, an arylcarboxylic ester, a haloalkoxy, a sulfonamido, an alkylsulfonamido, an arylsulfonamido, a sulfonic ester, a urea, a phosphoryl, a nitro, —T—Q, or $R_e$ and $R_f$ are —$(C(R_e)(R_f))_k$—T—O, wherein $R_e$ and $R_f$ are as defined herein, or $R_e$ and $R_f$ taken together with the carbons to which they are attached form a carbonyl, a methanthial, a heterocyclic ring, a cycloalkyl group or a bridged cycloalkyl group; Q is —NO or —$NO_2$; and T is independently a covalent bond, a carbonyl, an oxygen, —$S(O)_o$— or —$N(R_a)R_i$—, wherein o is an integer from 0 to 2, $R_a$ is a lone pair of electrons, a hydrogen or an alkyl group; $R_i$ is a hydrogen, an alkyl, an aryl, an alkylcarboxylic acid, an aryl carboxylic acid, an alkylcarboxylic ester, an arylcarboxylic ester, an alkylcarboxamido, an arylcarboxamido, an alkylaryl, an alkylsulfinyl, an alkylsulfonyl, an arylsulfinyl, an arylsulfonyl, a sulfonamido, a carboxamido, a carboxylic ester, an amino alkyl, an amino aryl, —$CH_2$—$C(T$—$Q)(R_e)(R_f)$, or —$(N_2O_2$—$)^-.M^+$, wherein $M^+$ is an organic or inorganic cation; with the proviso that when $R_i$ is —$CH_2$—$C(T$—$Q)(R_e)(R_f)$ or —$(N_2O_2$—$).M^+$; then "—T—Q" can be a hydrogen, an alkyl group, an alkoxyalkyl group, an aminoalkyl group, a hydroxy group or an aryl group.

In cases where $R_e$ and $R_f$ are a heterocyclic ring or $R_e$ and $R_f$ when taken together with the carbon atoms to which they are attached are a heterocyclic ring, then $R_i$ can be a substituent on any disubstituted nitrogen contained within the radical wherein $R_i$ is as defined herein.

Nitrosothiols can be prepared by various methods of synthesis. In general, the thiol precursor is prepared first, then converted to the S-nitrosothiol derivative by nitrosation of the thiol group with $NaNO_2$ under acidic conditions (pH is about 2.5) which yields the S-nitroso derivative. Acids which can be used for this purpose include aqueous sulfuric, acetic and hydrochloric acids. The thiol precursor can also be nitrosylated by reaction with an organic nitrite such as tert-butyl nitrite, or a nitrosonium salt such as nitrosonium tetraflurorborate in an inert solvent.

Another group of NO adducts for use in the present invention, where the NO adduct is a compound that donates, transfers or releases nitric oxide, include compounds comprising at least one ON—O—, ON—N— or ON—C— group. The compounds that include at least one ON—O—, ON—N— or ON—C— group are preferably ON—O—, ON—N— or ON—C-polypeptides (the term "polypeptide" includes proteins and polyamino acids that do not possess an ascertained biological function, and derivatives thereof); ON—O, ON—N— or ON—C-amino acids (including natural and synthetic amino acids and their stereoisomers and racemic mixtures); ON—O—, ON—N— or ON—C-sugars; ON—O—, ON—N— or ON—C— modified or unmodified oligonucleotides (comprising at least 5 nucleotides, preferably 5–200 nucleotides); ON—O—, ON—N— or ON—C— straight or branched, saturated or unsaturated, aliphatic or aromatic, substituted or unsubstituted hydrocarbons; and ON—O—, ON—N— or ON—C— heterocyclic compounds.

Another group of NO adducts for use in the present invention include nitrates that donate, transfer or release nitric oxide, such as compounds comprising at least one $O_2N$—O—, $O_2N$—N—, $O_2N$—S— or $O_2N$—C— group. Preferred among these compounds are $O_2N$—O—, $O_2N$—N—, $O_2N$—S— or $O_2N$—C— polypeptides (the term "polypeptide" includes proteins and also polyamino acids that do not possess an ascertained biological function, and derivatives thereof); $O_2N$—O—, $O_2N$—N—, $O_2N$—S— or $O_2N$—C— amino acids (including natural and synthetic amino acids and their stereoisomers and racemic mixtures); $O_2N$—O—, $O_2N$—N—, $O_2N$—S— or $O_2N$—C-sugars; $O_2N$—O—, $O_2N$—N—, $O_2N$—S— or $O_2N$—C— modified and unmodified oligonucleotides (comprising at least 5 nucleotides, preferably 5–200 nucleotides); $O_2N$—O—, $O_2N$—N—, $O_2N$—S— or $O_2N$—C— straight or branched, saturated or unsaturated, aliphatic or aromatic, substituted or unsubstituted hydrocarbons; and $O_2N$—O—, $O_2N$—N—, $O_2N$—S— or $O_2N$—C— heterocyclic compounds. Preferred examples of compounds comprising at least one $O_2N$—O—, $O_2N$—N—, $O_2N$—S— or $O_2N$—C— group include isosorbide dinitrate, isosorbide mononitrate, clonitrate, erythrityltetranitrate, mannitol hexanitrate, nitroglycerin, pentaerythritoltetranitrate, pentrinitrol and propatylnitrate.

Another group of NO adducts are N-oxo-N-nitrosoamines that donate, transfer or release nitric oxide and are represented by the formula: $R^1R^2N$—$N(O$—$M^+)$—NO, wherein $R^1$ and $R^2$ are each independently a polypeptide, an amino acid, a sugar, a modified or unmodified oligonucleotide, a straight or a branched, saturated or unsaturated aliphatic or aromatic, substituted or unsubstituted hydrocarbon, or a heterocyclic group, and $M^+$ is as defined herein.

Another group of NO adducts are thionitrates that donate, transfer or release nitric oxide and are represented by the formula: $R^1$—$(S)$—$NO_2$, where $R_1$ is a polypeptide, an amino acid, a sugar, a modified or unmodified oligonucleotide, a straight or branched, saturated or unsaturated, aliphatic or aromatic, substituted or unsubstituted hydrocarbon, or a heterocyclic group. Preferred are those compounds where $R^1$ is a polypeptide or hydrocarbon with a pair or pairs of thiols that are sufficiently structurally proximate, i.e., vicinal, that the pair of thiols will be reduced to a disulfide. Compounds which form disulfide species release nitroxyl ion (NO–) and uncharged nitric oxide (NO.).

The present invention is also directed to compounds that stimulate endogenous NO or elevate levels of endogenous endothelium-derived relaxing factor (EDRF) in vivo or are substrates for the enzyme, nitric oxide synthase. Such compounds include, for example, L-arginine, L-homoarginine, and N-hydroxy-L-arginine, including their nitrosated and nitrosylated analogs (e.g., nitrosated L-arginine, nitrosylated L-arginine, nitrosated N-hydroxy-L-arginine, nitrosylated N-hydroxy-L-arginine, nitrosated L-homoarginine and nitrosylated L-homoarginine), precursors of L-arginine and/or physiologically acceptable salts thereof, including, for example, citrulline, ornithine, glutamine, lysine, polypeptides comprising at least one of these amino acids, inhibitors of the enzyme arginase (e.g., N-hydroxy-L-arginine and 2(S)-amino-6-boronohexanoic acid) and the substrates for nitric oxide synthase, cytokines, adenosin, bradykinin, calreticulin, bisacodyl, and phenolphthalein. EDRF is a vascular relaxing factor secreted by the endothelium, and has been identified as nitric oxide (NO) or a closely related derivative thereof (Palmer et al, Nature, 327:524–526 (1987); Ignarro et al, Proc. Natl. Acad. Sci. USA, 84:9265–9269 (1987)).

The present invention is also directed to prostaglandins, preferably $PGE_1$ compounds, that are used in combination with NO donors, including those described herein, preferably with S-nitrosothiol compounds. $PGE_1$ compounds include, but are not limited to, alprostadil, misoprostol, misoprostol acid and enprostil, and their α-cyclodextrin complexes. Alprostadil (i.e., 7-(5-((1E)(3S)-3-hydroxyoct-1-enyl)(1R,4R,5R)-4-(hydroxy-2-oxocyclopentyl)heptanoic acid)), the most preferred $PGE_1$ compound, is represented by formula (II):

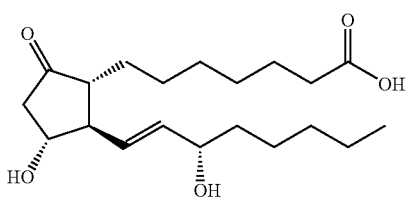

(II)

Alprostadil can be provided in a free-acid form or in the form of a pharmaceutically acceptable salt, as described herein. Alprostadil is commercially available, for example, in the form of a sterile powder for intracavemosal injection under the trade name CAVERJECT® (Pharmacia & Upjohn Company, Kalamazoo, Mich.) and in the form of a urethral suppository under the trade name MUSE® (Vivus Incorporated, Mountain View, Calif.).

The prostaglandins are more fully described in the literature, such as in Goodman and Gilman, The Pharmacological Basis of Therapeutics (9th Ed.), McGraw-Hill, Inc. (1996), The Physician's Desk Reference (49th Ed.), Medical Economics (1995), Drug Facts and Comparisons (1993 Ed), Facts and Comparisons (1993), Merck Index on CD-ROM, Twelfth Edition, Version 12:1, (1996), STN Express, file phar and file registry, the disclosures of each of which are incorporated herein by reference in their entirety.

The S-nitrosothiol compounds can release nitric oxide or otherwise directly or indirectly deliver or transfer nitric oxide to an intended site of activity, such as on a cell membrane in vivo. The term "nitric oxide" encompasses uncharged nitric oxide (NO.) and charged nitrogen monoxide species, preferably charged nitrogen monoxide species, such as nitrosonium ion ($NO^+$) and nitroxyl ion (NO–). S-nitrosothiol compounds are potent smooth muscle relaxants. U.S. Pat. No. 5,380,758 discloses the use of S-nitrosothiol compounds for relaxing vascular and non-vascular smooth muscle. U.S. Pat. No. 5,648,393 discloses the treatment and prevention of male impotence by administering S-nitrosothiol compounds. The disclosures of each of these patents are incorporated herein by reference in their entirety In the present invention, S-nitrosothiol compounds, include, for example, S-nitrosoglutathione, S-nitroso-N-acetylcysteine, S-nitrosocysteine, S-nitrosohomocysteine, S-nitrosopenicillamine, S-nitrosocaptopril, and the like. The preferred S-nitrosothiol compound is S-nitrosoglutathione (GS—NO), which is represented by formula (III):

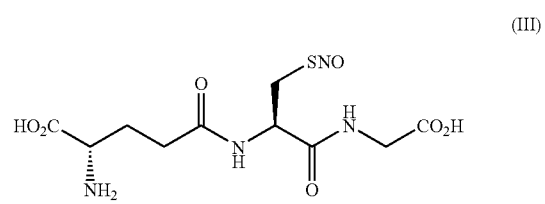

(III)

S-nitrosoglutathione can be provided in a free-acid or free-base form or in the form of a pharmaceutically acceptable salt. S-nitrosoglutathione is commercially available from, for example, Sigma Chemical Company (St. Louis, Mo.); Cayman Chemical (Ann Arbor, Mich.); Calbiochem-Novabiochem (San Diego, Calif.); Precision Biochemicals, Inc. (Vancouver, British Columbia); and Toronto Research Chemicals, Inc. (Ontario, Canada). S-nitrosoglutathione monomethyl ester is commercially available from, for example, Calbiochem-Novabiochem (San Diego, Calif.).

The present invention is also based on the discovery that the administration of a therapeutically effective amount of the compounds and compositions described herein is effective for treating or preventing sexual dysfunctions or enhancing sexual responses in patients, including males and females. For example, the patient can be administered a therapeutically effective amount of at least one nitrosated and/or nitrosylated prostaglandin of the present invention. In another embodiment, the patient can be administered a therapeutically effective amount of at least one nitrosated and/or nitrosylated prostaglandin, and at least one compound that donates, transfers or releases nitric oxide, or elevates levels of endogenous EDRF or nitric oxide, or is a substrate for nitric oxide synthase. In yet another embodiment, the patient can be administered a therapeutically effective amount of at least one nitrosated and/or nitrosylated prostaglandin, and at least one vasoactive agent, and, optionally, at least one compound that donates, transfers or releases nitric oxide, or elevates levels of endogenous EDRF or nitric oxide, or is a substrate for nitric oxide synthase. The compounds can be administered separately or as components of the same composition.

A vasoactive agent is any therapeutic agent capable of relaxing vascular smooth muscle. Suitable vasoactive agents include, but are not limited to, potassium channel activators (such as, for example, nicorandil, pinacidil, cromakalim, minoxidil, aprilkalim, loprazolam and the like); calcium channel blockers (such as, for example, nifedipine, verapamril, diltiazem, gallopamil, niludipine, nimodipins, nicardipine, and the like); β-blockers (such as, for example, butixamine, dichloroisoproterenol, propanolol, alprenolol, bunolol, nadolol, oxprenolol, perbutolol, pinodolol, sotalol, timolol, metoprolol, atenolol, acebutolol, bevantolol, pafenolol, tolamodol, and the like); long and short acting α-adrenergic receptor antagonist (such as, for example, phenoxybenzamide, dibenamine, doxazosin, terazosin, phentolamine, tolazoline, prozosin, trimazosin, yohimbine, moxisylyte and the like); phosphodiesterase inhibitors (such as, for example, papaverine, zaprinast, sildenafil, IC 351); adenosine, ergot alkaloids (such as, for example, ergotamine, ergotamine analogs, including, for example, acetergamine, brazergoline, bromerguride, cianergoline, delorgotrile, disulergine, ergonovine maleate, ergotamine tartrate, etisulergine, lergotrile, lysergide, mesulergine, metergoline, metergotamine, nicergoline, pergolide, propisergide, proterguride, terguride and the like); vasoactive intestinal peptides (such as, for example, peptide histidine isoleucine, peptide histidine methionine, substance P, calcitonin gene-related peptide, neurokinin A, bradykinin, neurokinin B, and the like); dopamine agonists (such as, for example, apomorphine, bromocriptine, testosterone, cocaine, strychnine, and the like); opioid antagonists (such as, for example, naltrexone, and the like); endothelin antagonists (such as, for example, bosentan, sulfonamide endothelin antagonists, BQ-123, SQ 28608, and the like) and mixtures thereof. Preferred are combinations of at least one nitrosated and/or nitrosylated prostaglandins (such as, for example, alprostadil, misoprostol and/or enprostil,) with at least one α-blocker (such as, for example, phentolamine, prazosin, doxazosin, terazosin, yohimbine and/or moxisylyte) and/or at least one PDE inhibitor (such as, for example, papaverine, zaprinast and/or sildenafil).

Another embodiment of the present invention provides methods for treating and/or preventing sexual dysfunctions and/or enhancing sexual responses in a patient in need thereof by administering to the patient a therapeutically effective amount of at least one prostaglandin and at least one S-nitrosothiol compound, and, optionally, at least one vasoactive agent. The compounds can be administered separately or as components of the same composition. The prostaglandin can be any prostaglandin described herein, preferably a $PGE_1$ compound, more preferably alprostadil. The S-nitrosothiol compound can be any S-nitrosothiol compound described herein, preferably S-nitrosoglutathione.

The treatment and/or prevention of sexual dysfunctions and/or enhancement of sexual responses in patients using prostaglandins in combination with nitric oxide donors has been previously described. For example, Tordjman, *Contracept. Fertil. Sex*, 21(6):509–510 (1993), describes the use of $PGE_1$ in combination with nitric oxide for the treatment of impotence; U.S. Pat. No. 5,492,911 describes the treatment of sexual impotence in humans by administering linsidomine in combination with one or more prostaglandins; WO 97/39760 describes methods for enhancing penile or clitoral erection with minimal or no pain by administering a smooth muscle relaxing agent, such as $PGE_1$, in combination with an NO donor; U.S. Pat. No. 5,877,216 describes the use of prostaglandins in combination with nitric oxide releasing agents for the treatment of female sexual dysfunction. The disclosure of each of these patents, applications and publications is incorporated by reference herein in their entirety. None of these references, however, disclose, suggest or provide motivation to combine a prostaglandin (preferably $PGE_1$, more preferably alprostadil) with an S-nitrosothiol compound (particularly S-nitrosoglutathione) for treating or preventing sexual dysfunctions, and none of these references disclose or suggest the synergistic or superior effects that are unexpectedly achieved by combining a prostaglandin (preferably $PGE_1$, more preferably alprostadil) with an S-nitrosothiol compound (preferably S-nitrosoglutathione) for treating or preventing sexual dysfunctions, as described and claimed herein.

Another embodiment of the present invention provides methods to prevent or treat cerebrovascular disorders (Chemtob et al, *Acta Paediatr.*, 85(5):517–524 (1996), Kadoi et al, *Anesth Analg*, 85(5):1054–1059 (1997)); cardiovascular disorders (Utoh et al, *Int. J. Angiology*, 7(3): 228–230 (1998)); benign prostatic hyperplasia (BPH) (Rolland et al, *Eur Urol.*, 7(1):41–45 (1981)), glaucoma (Camras et al, *Am. J. Ophthalmol.*, 126(3):390–399 (1998), Alm, *Prog. Retin. Eye Res.*, 17(3):291–312 (1998)); organ transplants (Muller et al, *Adv. Exp. Med. Biol.*, 433:9–12 (1997), Merion, *Adv. Exp. Med. Biol.*, 433:13–18 (1997), Iberer et al *Adv. Exp. Med. Biol.*, 433:19–22 (1997)); peptic ulcers (Scheimam et al, *Am. J. Med.*, 105(5A):32S–38S (1998)); and to induce abortions (Grimes, *Obstet Gynecol.*, 89:790–796 (1997), Atlas et al, *Obstet Gynecol.*, 92(3): 398–402 (1998)); and in WO 98/58910 by administering to a patient in need thereof a therapeutically effective amount of the compounds and/or compositions described herein. These methods may further comprise administering at least one vasoactive agent, as described herein. For example, the patient can be administered a therapeutically effective amount of at least one nitrosated and/or nitrosylated prostaglandin of the present invention. In another embodiment, the patient can be administered a therapeutically effective amount of at least one nitrosated and/or nitrosylated prostaglandin, and at least one compound that donates, transfers or releases nitric oxide, or elevates levels of endogenous EDRF or nitric oxide or is a substrate for nitric oxide synthase. In yet another embodiment, the patient can be administered a therapeutically effective amount of at least one nitrosated and/or nitrosylated prostaglandin, and at least one vasoactive agent, and, optionally, at least one compound that donates, transfers or releases nitric oxide, or elevates levels of endogenous EDRF or nitric oxide, or is a substrate for nitric oxide synthase. In still yet another embodiment, the patient can be administered a therapeutically effective amount of at least one prostaglandin and at least one S-nitrosothiol compound, and, optionally, at least one vasoactive agent. The compounds and compositions of the present invention can also be administered in combination with other medications used for the treatment of these disorders.

When administered in vivo, the compounds and compositions of the present invention can be administered in combination with pharmaceutically acceptable carriers and in dosages described herein. When the compounds and compositions of the present invention are administered as a mixture of at least one nitrosated and/or nitrosylated prostaglandin and at least one nitric oxide donor, or at least one prostaglandin and at least one S-nitrosothiol compound, they can also be used in combination with one or more additional compounds which are known to be effective against the specific disease state targeted for treatment (e.g., vasoactive agents). The nitric oxide donor(s), S-nitrosthiol compound and/or vasoactive agents can be administered simultaneously with, subsequently to, or prior to administration of the prostaglandin(s) and/or other additional compound(s).

The compounds and compositions of the present invention can be administered by any available and effective delivery system including, but not limited to, orally, bucally, parenterally, by inhalation spray, by topical application, by injection into the corpus cavernosum tissue, by transurethral drug delivery, transdermally, vaginally, or rectally (e.g., by the use of suppositories) in dosage unit formulations containing conventional nontoxic pharmaceutically acceptable carriers, adjuvants, and vehicles, as desired. Parenteral includes subcutaneous injections, intravenous injections, intramuscular injections, intrasternal injections, and infusion techniques. Parenteral also includes injection into the corpus cavernosum tissue, which can be conducted using any effective injection system including, but not limited to, conventional syringe-and-needle systems or needleless injection devices.

Transdermal drug administration, which is known to one skilled in the art, involves the delivery of pharmaceutical agents via percutaneous passage of the drug into the systemic circulation of the patient. Topical administration, which is well known to one skilled in the art, involves the delivery of pharmaceutical agents via percutaneous passage of the drug into the systemic circulation of the patient. Topical administration includes vaginal administration, vulval administration, penile administration and rectal administration. Topical administration can also involve transdermal patches or iontophoresis devices. Other components can be incorporated into the transdermal patches as well. For example, compositions and/or transdermal patches can be formulated with one or more preservatives or bacteriostatic agents including, but not limited to, methyl hydroxybenzoate, propyl hydroxybenzoate, chlorocresol, benzalkonium chloride, and the like. Topical administration also includes administering the compounds and compositions to the eyes, particularly for the treatment of glaucoma.

Dosage forms for topical administration of the compounds and compositions of the present invention preferably include creams, sprays, lotions, gels, ointments, emulsions, coatings for condoms, liposomes, foams, and the like. Administration of the cream, spray, lotion, gel, ointment, emulsion, coating, liposome, or foam can be accompanied by the use of an applicator or by transurethral drug delivery using a syringe with or without a needle or penile insert or device, or by clitoral, vulval or vaginal delivery, and is within the skill of the art. Typically a lubricant and/or a local anesthetic for desensitization can also be included in the formulation or provided for use as needed. Lubricants include, for example, K-Y jelly (available from Johnson & Johnson) or a lidocaine jelly, such as XYLOCAINE® 2% jelly (available from Astra Pharmaceutical Products). Local anesthetics include, for example, novocaine, procaine, tetracaine, benzocaine and the like.

Solid dosage forms for oral administration can include capsules, tablets, effervescent tablets, chewable tablets, pills, powders, sachets, granules and gels. In such solid dosage forms, the active compounds can be admixed with at least one inert diluent such as sucrose, lactose or starch. Such dosage forms can also comprise, as in normal practice, additional substances other than inert diluents, e.g., lubricating agents such as magnesium stearate. In the case of capsules, tablets, effervescent tablets, and pills, the dosage forms can also comprise buffering agents. Soft gelatin capsules can be prepared to contain a mixture of the active compounds or compositions of the present invention and vegetable oil. Hard gelatin capsules can contain granules of the active compound in combination with a solid, pulverulent carrier such as lactose, saccharose, sorbitol, mannitol, potato starch, corn starch, amylopectin, cellulose derivatives of gelatin. Tablets and pills can be prepared with enteric coatings.

Liquid dosage forms for oral administration can include pharmaceutically acceptable emulsions, solutions, suspensions, syrups, and elixirs containing inert diluents commonly used in the art, such as water. Such compositions can also comprise adjuvants, such as wetting agents, emulsifying and suspending agents, and sweetening, flavoring, and perfuming agents.

Suppositories for vaginal or rectal administration of the compounds and compositions of the invention can be prepared by mixing the compounds or compositions with a suitable nonirritating excipient such as cocoa butter and polyethylene glycols which are solid at room temperature but liquid at body temperature, such that they will melt and release the drug.

Injectable preparations, for example, sterile injectable aqueous or oleaginous suspensions can be formulated according to the known art using suitable dispersing agents, wetting agents and/or suspending agents. The sterile injectable preparation can also be a sterile injectable solution or suspension in a nontoxic parenterally acceptable diluent or solvent, for example, as a solution in 1,3-butanediol. Among the acceptable vehicles and solvents that can be used are water, Ringer's solution, and isotonic sodium chloride solution. Sterile fixed oils are also conventionally used as a solvent or suspending medium.

The compounds and compositions of the present invention will typically be administered in a pharmaceutical composition containing one or more carriers or excipients, i.e., pharmaceutically acceptable organic or inorganic carrier substances suitable for parenteral application which do not deleteriously react with the active compounds. Examples of pharmaceutically acceptable carriers include, for example, water, salt solutions, alcohol, silicone, waxes, petroleum jelly, vegetable oils, polyethylene glycols, propylene glycol, liposomes, sugars, gelatin, lactose, amylose, magnesium stearate, talc, surfactants, silicic acid, viscous paraffin, perfume oil, fatty acid monoglycerides and diglycerides, petroethral fatty acid esters, hydroxymethyl-cellulose, polyvinylpyrrolidone, and the like. The compositions can also include one or more permeation enhancers including, for example, dimethylsulfoxide (DMSO), dimethyl formamide (DMF), N,N-dimethylacetamide (DMA), decylmethylsulfoxide (C10MSO), polyethylene glycol monolaurate (PEGML), glyceral monolaurate, lecithin, 1-substituted azacycloheptan-2-ones, particularly 1-N-dodecylcyclazacylcoheptan-2-ones (available under the trademark Azone™ from Nelson Research & Development Co., Irvine, Calif.), alcohols and the like. The pharmaceutical preparations can be sterilized and if desired, mixed with auxiliary agents which do not deleteriously react with the active compounds, e.g., lubricants, preservatives, stabilizers, wetting agents, emulsifiers, salts for influencing osmotic pressure, buffers, colorings, flavoring and/or aromatic substances, and the like. For parenteral application, particularly suitable vehicles consist of solutions, preferably oily or aqueous solutions, as well as suspensions, emulsions, or implants. Aqueous suspensions may contain substances which increase the viscosity of the suspension and include, for example, sodium carboxymethyl cellulose, sorbitol and/or dextran. Optionally, the suspension may also contain stabilizers.

The composition, if desired, can also contain minor amounts of wetting agents, emulsifying agents and/or pH buffering agents. The composition can be a liquid solution, suspension, emulsion, tablet, pill, capsule, sustained release formulation, or powder. The composition can be formulated as a suppository, with traditional binders and carriers such as triglycerides. Oral formulations can include standard carriers such as pharmaceutical grades of mannitol, lactose, starch, magnesium stearate, sodium saccharine, cellulose, magnesium carbonate, and the like.

Various delivery systems are known and can be used to administer the compounds or compositions of the present invention, including, for example, encapsulation in liposomes, microbubbles, emulsions, microparticles, microcapsules and the like. The required dosage can be administered as a single unit or in a sustained release form.

The bioavailabilty of the compositions can be enhanced by micronization of the formulations using conventional techniques such as grinding, milling, spray drying and the like in the presence of suitable excipients or agents such as phospholipids or surfactants.

The compounds and compositions of the present invention can be formulated as pharmaceutically acceptable salts. Pharmaceutically acceptable salts include, for example, alkali metal salts and addition salts of free acids or free bases. The nature of the salt is not critical, provided that it is pharmaceutically-acceptable. Suitable pharmaceutically-acceptable acid addition salts may be prepared from an inorganic acid or from an organic acid. Examples of such inorganic acids include, but are not limited to, hydrochloric, hydrobromic, hydroiodic, nitric (nitrate salt), nitrous (nitrite salt), carbonic, sulfuric and phosphoric acid and the like. Appropriate organic acids include, but are not limited to, aliphatic, cycloaliphatic, aromatic, heterocyclic, carboxylic and sulfonic classes of organic acids, such as, for example, formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, salicylic, p-hydroxybenzoic, phenylacetic, mandelic, embonic (pamoic), methanesulfonic, ethanesulfonic, benzenesulfonic, pantothenic, toluenesulfonic, 2-hydroxyethanesulfonic, sulfanilic, stearic, algenic, β-hydroxybutyric, cyclohexylaminosulfonic, galactaric and galacturonic acid and the like. Suitable pharmaceutically-acceptable base addition salts include, but are not limited to, metallic salts made from aluminum, calcium, lithium, magnesium, potassium, sodium and zinc or organic salts made from primary, secondary and tertiary amines, cyclic amines, N,N'-dibenzylethylenediamine, chloroprocaine, choline, diethanolamine, ethylenediamine, meglumine (N-methylglucamine) and procaine and the like. All of these salts may be prepared by conventional means from the corresponding compound by reacting, for example, the appropriate acid or base with the compound.

"Therapeutically effective amount" refers to the amount of the nitrosated and/or nitrosylated prostaglandin, prostaglandin, nitric oxide adduct and/or vascoactive agent which is effective to achieve its intended purpose. While individual patient needs may vary, determination of optimal ranges for effective amounts of each nitric oxide adduct is within the skill of the art. Generally the dosage regimen for treating a condition with the compounds and/or compositions of this invention is selected in accordance with a variety of factors, including the type, age, weight, sex, diet and medical condition of the patient, the severity of the dysfunction, the route of administration, pharmacological considerations such as the activity, efficacy, pharmacokinetic and toxicology profiles of the particular compound used, whether a drug delivery system is used, and whether the compound is administered as part of a drug combination and can be adjusted by one skilled in the art. Thus, the dosage regimen actually employed may vary widely and therefore may deviate from the preferred dosage regimen set forth herein.

The amount of a given prostaglandin which will be effective in the treatment of a particular dysfunction or condition will depend on the nature of the dysfunction or condition, and can be determined by standard clinical techniques, including reference to Goodman and Gilman, supra; The Physician's Desk Reference, supra; Medical Economics Company, Inc., Oradell, N.J., 1995; and Drug Facts and Comparisons, Inc., St. Louis, Mo., 1993. The precise dose to be used in the formulation will also depend on the route of administration, and the seriousness of the dysfunction or disorder, and should be decided by the physician and the patient's circumstances.

The nitrosated and/or nitrosylated prostaglandins of the invention are used at dose ranges and over a course of dose regimen and are administered in the same or substantially equivalent vehicles/carrier by the same or substantially equivalent as their non-nitrosated/nitrosylated counterparts. The nitrosated and/or nitrosylated compounds of the invention can also be used in lower doses and in less extensive regimens of treatment. The amount of active ingredient that may be combined with the carrier materials to produce a single dosage form will vary depending upon the host treated and the particular mode of administration.

The usual doses of prostaglandins are about 0.001 mg to 1 mg and preferably 0.01 mg to about 0.1 mg for intracavernosal administration per injection. For transurethral administration, the dose of prostaglandins is about 0.01 mg to about 10 mg, preferably 0.1 mg to 1 mg. For transdermal administration, the dose of prostaglandinis about 0.1 mg to 10 mg.

The doses of nitric oxide donors in the pharmaceutical composition can be in amounts of about 0.001 mg to about 6 g and the actual amount administered will be dependent on the specific nitric oxide donor. For example, when L-arginine is the nitric oxide donor, the dose is about 2 g/day to about 6 g/day, preferably about 3 g/day, administered orally at least one hour prior to sexual activity. Effective doses may be extrapolated from dose-response curves derived from in vitro or animal model test systems and are in the same ranges or less than as described for the commercially available compounds in the Physician's Desk Reference, supra.

In the methods of administering a prostaglandin in combination with an S-nitrosothiol, the prostaglandin, such as alprostadil, is administered by intracavernosal injection in an amount of about 1 μg to about 40 μg, preferably about 2.5 μg to about 20 μg, more preferably about 2.5 μg to about 10 μg per injection. For transurethral administration, the dose of prostaglandin, such as alprostadil, is about 100 μg to about 1 mg, preferably about 125 μg to about 750 μg. For topical administration, the dose of prostaglandin, such as alprostadil, is about 1 μg to about 5 mg, preferably about 20 μg to about 2 mg.

Also in the methods of administering a prostaglandin in combination with an S-nitrosothiol, the S-nitrosothiol compound, such as S-nitrosoglutathione, is administered by intracavernosal injection in an amount of about 10 μg to about 5 mg, preferably about 100 μg to about 2 mg, more preferably about 500 μg to about 2 mg per injection. For transurethral administration, the dose of S-nitrosothiol, such as S-nitrosoglutathione, is about 1 mg to about 100 mg, preferably about 20 mg to about 75 mg. For topical administration, the dose of S-nitrosothiol, such as S-nitrosoglutathione, is about 5 mg to about 1 g, preferably about 10 mg to about 750 mg.

In one embodiment of the present invention, the prostaglandin (such as a $PGE_1$, more particularly alprostadil) and the S-nitrosothiol compound (such as S-nitrosoglutathione) are administered as separate components. Preferably, the prostaglandin (such as $PGE_1$, more particularly alprostadil) for the treatment of male sexual dysfunction is administered in the form of a sterile powder; and the S-nitrosothiol compound (such as S-nitrosoglutathione) is also prepared in the form of a sterile powder. The powders are separately reconstituted in bacteriostatic water for injection or sterile water, both preserved with benzyl alcohol. When the prostaglandin and S-nitrosothiol compounds are administered as separate components in the methods of the present invention, they are preferably administered to the patient at about the same time. "About the same time" means that within about thirty minutes of administering one compound (e.g., the prostaglandin or the S-nitrosothiol compound) to the patient, the other compound (e.g., S-nitrosothiol compound or the prostaglandin) is administered to the patient. "About the same time" also includes simultaneous administration of the compounds.

In another embodiment of the present invention, for the treatment of male sexual dysfunction, the prostaglandin (such as $PGE_1$, more particularly alprostadil) and the S-nitrosothiol compound (such as S-nitrosoglutathione) are components in the same composition. The composition can be in the form of a sterile powder, wherein the powder is reconstituted prior to injection in to the corpus cavernosum.

In another embodiment of the present invention, for the treatment of female sexual dysfunction, the prostaglandin (such as alprostadil) and the S-nitrosothiol compound (such as S-nitrosoglutathione) are components in the same composition for topical application. The composition can be in the form of a gel, spray, ointment, cream, emulsion, lotion, solid, solution, suspension, foam, suppository, coating for a condom or liposome composition.

While the compounds and/or compositions of the present invention can be administered on a regular basis (e.g., daily), they are preferably administered as a single dose prior to sexual activity or sexual intercourse. Such single dose administration prior to sexual activity or sexual intercourse allows for the prevention and/or treatment of a sexual dysfunction in a patient and/or enhances sexual responses in a patient. For example, in the methods of the present invention, the compounds and/or compositions are generally administered about 1 minute to about 60 minutes prior to sexual activity or sexual intercourse; preferably about 2 minutes to about 20 minutes prior to sexual activity or sexual intercourse; more preferably about 5 minutes to about 10 minutes prior to sexual activity or sexual intercourse.

The present invention also provides pharmaceutical kits comprising one or more containers filled with one or more of the ingredients of the pharmaceutical compounds and/or compositions of the present invention, including, at least one nitrosated and/or nitrosylated prostaglandin, and one or more of the NO donors, and one or more vasoactive agents described herein. Such kits can also include, for example, other compounds and/or compositions (e.g., permeation enhancers, lubricants, and the like), a device(s) for administering the compounds and/or compositions, and written instructions in a form prescribed by a governmental agency regulating the manufacture, use or sale of pharmaceuticals or biological products, which instructions can also reflects approval by the agency of manufacture, use or sale for human administration.

EXAMPLES

The following non-limiting examples are for purposes of illustration only and are not intended to limit the scope of the invention or claims.

In the examples, $PGE_1$ (specifically alprostadil or 7-[5-((1E)(3S)-3-hydroxyoct-1-enyl)(1R,4R,5R)-4-(hydroxy-2-oxocyclopentyl)heptanoate) was obtained from Upjohn (Belgium) for Example 1 to 7 and from Cayman Chemical (Ann Arbor, Mich.) for Example 8 to 14. GS—NO was prepared according to Example 1. The drugs were dissolved in distilled water, except $PGE_1$, which was dissolved at a concentration of 10 mM in ethanol. Dilutions were made in distilled water at the time of the experiment.

Example 1

Preparation of S-Nitrosoglutathione

Glutathione (N—(N—L—γ-glutamyl-L-cysteinyl)glycine) (100 g, 0.325 mol) was dissolved in deoxygenated water (200 ml) and 2N HCl (162 ml) at room temperature and then the reaction mixture was cooled to 0° C. With rapid stirring, a solution of sodium nitrite (24.4 g, 0.35 mol) in water (40 ml) was added. Stirring with cooling of the reaction mixture was continued for approximately 1 hour, after which time the pink precipitate which formed was collected by vacuum filtration. The filter cake was resuspended in chilled 40% acetone-water (600 ml) and collected by vacuum filtration. The filter cake was washed with acetone (2×200 ml) and ether (100 ml) and then dried under high vacuum at room temperature in the dark to afford the title compound, N—(N—L—γ-glutamyl-S-Nitroso-L-cysteinyl)glycine, as a pink powder. $^1$H NMR ($D_2O$): δ1.98 (m, 2H), 2.32 (t, 2H), 3.67 (t, 1H), 3.82 (s, 2H), 3.86 (dd, 1H), 3.98 (dd, 1H), 4.53 (m, 1H).

Example 2

Preparation of Corpus Cavernosum Tissue

Human corpus cavernosum specimens were obtained from impotent men at the time of penile prosthesis insertion. Tissues were maintained at 4–6° C. in M-400 solution (composition per 100 ml: mannitol, 4.19 g; $KH_2PO_4$, 0.205 g; $K_2HPO_4.3H_2O$, 0.97 g; KCl, 0.112 g; $NaHCO_3$, 0.084 g) until used. Corpus cavernosum tissues were typically used between 2 and 16 hours from extraction.

Example 3

Measurement of cGMP in Human Corpus Cavernosum Tissues

Measurement of cyclic GMP in corpus cavernosal tissues was carried out as follows. Corpus cavernosal tissue strips (3×3×7 mm) were immersed in a 8 ml organ chamber containing physiological salt solution, maintained at 37° C. and aerated with 5% $CO_2$/95% air, pH 7.4. The tissues were then given 30 μM Zaprinast and 100 μM IBMX (3-isobutyl-1-methylxanthine, a cAMP specific phosphodiesterase inhibitor) and incubated for 15 minutes; then each tissue was incubated with the test drug (or control drug) at various concentrations or with vehicle (the buffer in which the drugs are delivered). Tissues were incubated for another 5 minutes then immediately frozen in liquid nitrogen and stored at −80° C. until extraction for cyclic nucleotide assay. Tissues were extracted by homogenization in 6% trichloroacetic acid followed by ether ($H_2O$-saturated) extraction and lyophilization. cGMP levels were determined by ELISA using a kit from Cayman Chemical (Ann Arbor, Mich.).

Protein concentration in the corpus cavernosum tissue was determined using the Bio-Rad Protein Assay Kit microtiter plate assay procedure (Bio-Rad, Hercules, Calif.) with bovine serum albumin as the standard.

The measured concentrations of cGMP in picomoles were normalized based on milligrams of protein to provide a valid comparison between each tissue sample. Statistical analysis were conducted using one way ANOVA analysis followed by Student-Newmann-Keuls post-hoc test using GraphPad InStat software for Apple computers.

As depicted in FIG. 1, the human corpus cavemosum tissue samples are capable of producing cGMP without the addition of a drug or other stimulating agent (Control). Addition of 1 µM $PGE_1$ alone did not produce a significant amount of cGMP when compared to the control. Addition of either 100 µM GS—NO alone or the combination of 1 µM $PGE_1$ and 100 µM GS—NO, resulted in the production of increased amounts of cGMP. This increased amount of cGMP production was demonstrated to be statistically significant compared to the control samples.

Example 4

Relaxation Studies of Human Corpus Cavernosum Tissues

Figure 2:
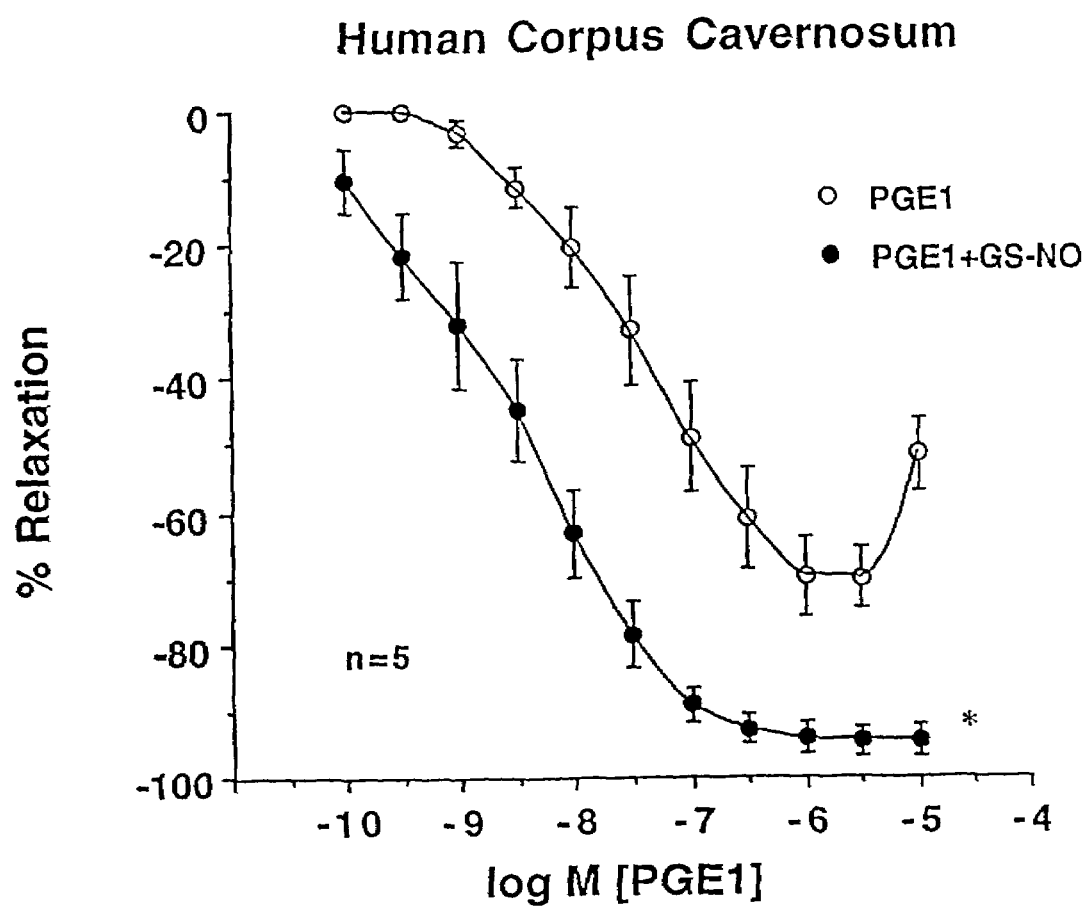
FIG. 2 is a concentration response curve in human corpus cavernosum tissue for $PGE_1$ alone and for the combination of $PGE_1$ and GS—NO. Tissues were incubated in a physiological salt solution, bubbled with 95% $O_2$, and treated with increasing concentrations of $PGE_1$ alone (open circles); or increasing concentrations of $PGE_1$ in the presence of GS—NO (closed circles). The GS—NO concentration was always 100 times greater than the concentration of $PGE_1$. The $PGE_1$ was alprostadil. 5 samples were measured for each condition tested (n=5). In the x-axis, log M [PGE$_1$] corresponds to ten fold increases of PGE$_1$ from 0.1 nM (at −10) to 10 μM (at −5). Data are expressed as mean standard error of the percentage of total relaxation induced by 0.1 mM papaverine hydrochloride. * P<0.01 by two-factor ANOVA analysis using StatView software for Apple computers.
Figure 3:
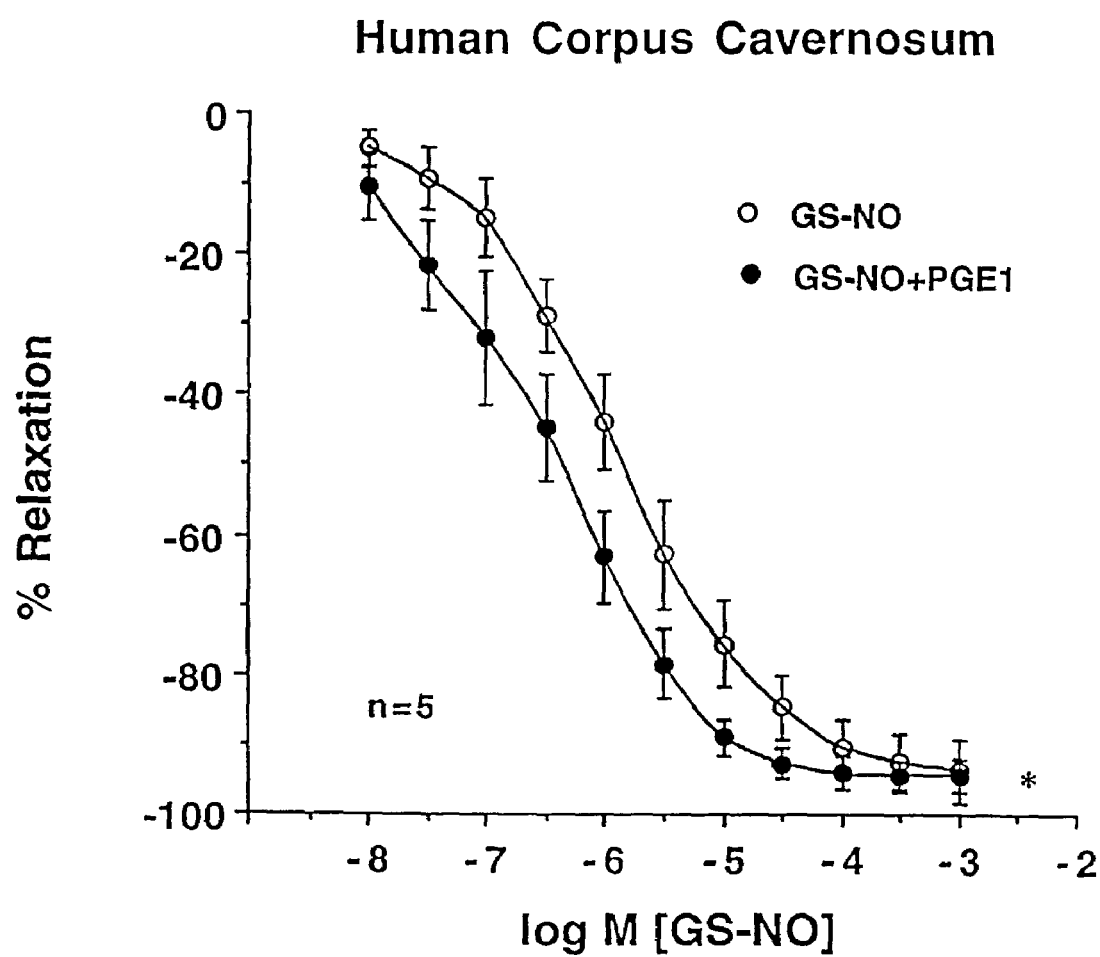
FIG. 3 is a concentration response curve in human corpus cavernosum tissue for GS—NO alone and for the combination of GS—NO and PGE$_1$. Tissues were incubated in a physiological salt solution, bubbled with 95% O$_2$, and treated with increasing concentrations of GS—NO alone (open circles); or increasing concentrations of GS—NO in the presence of PGE$_1$ (closed circles), where a total of 5 samples were tested (n=5). The GS—NO concentration was always 100 times greater than the concentration of PGE$_1$. In the x-axis, log M [GS—NO] corresponds to ten fold increases of GS—NO from 0.01 μM (at −8) to 1000 μM (at −3). Data are expressed as mean±standard error of the percentage of total relaxation induced by 0.1 mM papaverine hydrochloride. * P<0.01 by two-factor ANOVA analysis using StatView software for Apple computers.

Concentration response relaxation studies of human corpus cavernosum tissues were conducted as follows. Corpus cavernosal tissue strips (3×3×7 mm), obtained as described in Example 2, were immersed in a 8 ml organ chamber containing physiological salt solution, maintained at 37° C. and aerated with 5% $CO_2$/95% air, pH 7.4. Each strip was incrementally stretched to optimal isometric tension, as determined by maximal contractile responses to 1 µM phenylephrine. Relaxant responses were evaluated by adding increasing cumulative concentrations of compounds to the strips contracted with 0.5 µM phenylephrine. Relaxation responses were expressed as a percentage of total relaxation induced by the addition of 0.1 mM papaverine hydrochloride (total loss of tone) at the end of the experiment. In FIGS. 2 and 3, the data are expressed as mean±standard error. Statistical analysis were conducted using a two-factor ANOVA statistical analysis using StatView software for Apple computers.

Example 5

$PGE_1$ and GS—NO Concentration Response Relaxation Studies of Human Corpus Cavernosum Tissues The tissues were prepared according to Example 4. The percent relaxation induced by either increasing concentrations of $PGE_1$ alone or the combination of increasing concentrations of $PGE_1$ in the presence of GS—NO (constant concentration ratio of $PGE_1$:GS—NO is 1:100) were measured. As can be seen from FIG. 2, there was a significant shift to the left of the $PGE_1$ concentration-response curve with the co-administration of GS—NO. $EC_{50}$ (concentration required to obtain the half-maximum response induced by the compound) for $PGE_1$ alone was 0.083±0.05 µM compared to 0.006±0.001 µM for the combination of $PGE_1$ and GS—NO, p<0.01. In addition the maximum response produced by the combination of $PGE_1$ and GS—NO is greater than that of $PGE_1$ alone.

Example 6

GS—NO. Concentration Response Relaxation Studies of Human Corpus

Cavernosum Tissues

The tissues were prepared according to Example 4. The percent relaxation induced by either increasing concentrations of GS—NO alone or the combination of increasing concentrations of GS—NO in the presence of $PGE_1$ (constant concentration ratio of GS—NO:$PGE_1$ is 100:1) were measured. As can be seen from FIG. 3, there was a significant shift to the left of the GS—NO concentration-response curve with the co-administration of $PGE_1$. $EC_{50}$ for GS—NO alone was 2.56±1.3 µM compared to 0.58±0.16 µM for the combination of GS—NO and $PGE_1$, p<0.05.

Example 7

Determination of Synergy for the Combination of $PGE_1$ and GS—NO for the Relaxation of Human Corpus Cavernosum Tissue The effect of the combination of $PGE_1$ and GS—NO for the relaxation of the human corpus cavernosum tissue was calculated to be synergistic using the following formula (Berenbaum, *Pharmacol. Rev.*, 41:93–141 (1989)):

| | |
|---|---|
| $d_a/D_a + d_b/D_b < 1$ | synergy effect |
| $d_a/D_a + d_b/D_b = 1$ | zero interaction | where $d_a$ and $d_b$ are the concentrations of $PGE_1$ and GS—NO used in the combination which are required to obtain a specified level of the effect;

$D_a$ and $D_b$ are their single concentrations of $PGE_1$ and GS—NO, respectively, which were isoeffective with the combination ($d_a+d_b$) at any specified level of effect.

Figure 4:
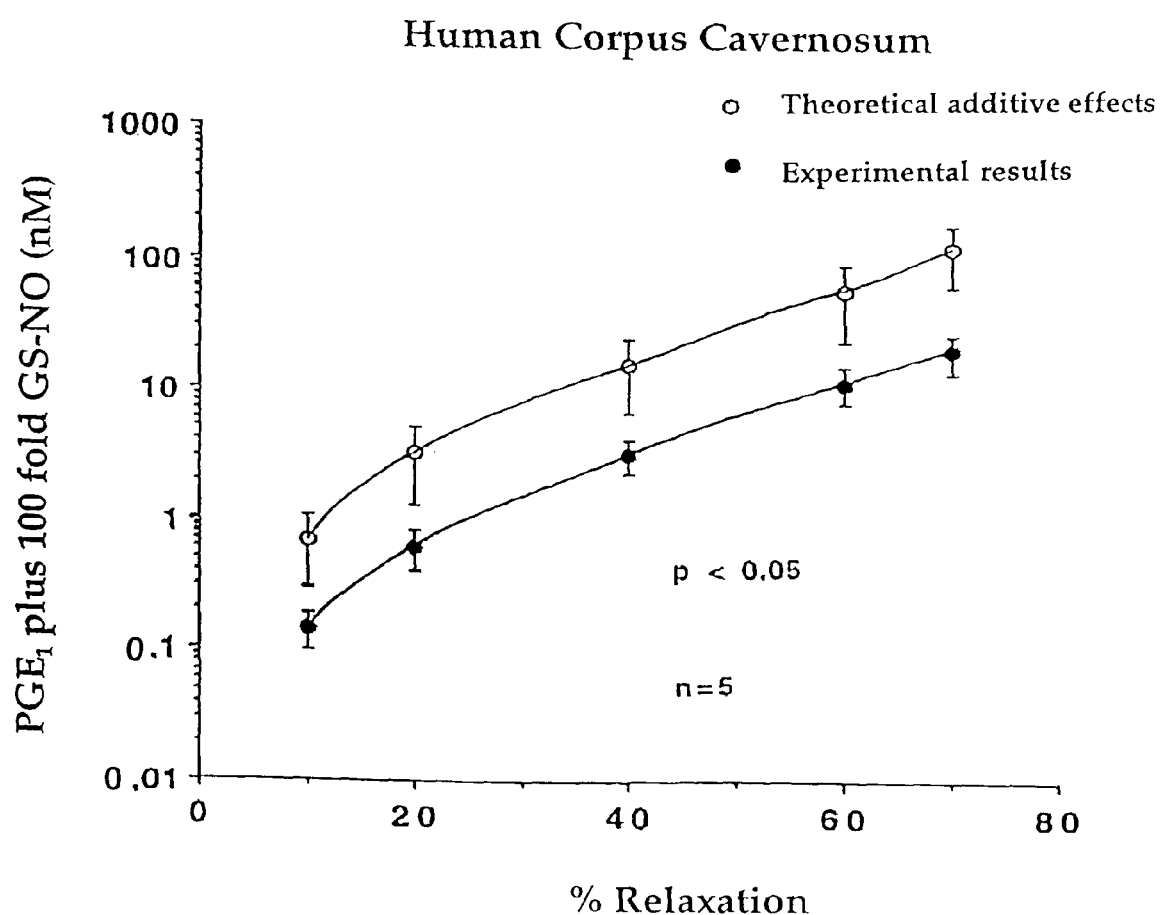
FIG. 4 is an analysis of the synergy elicited by the combination of PGE$_1$ and GS—NO in human corpus cavernosum tissue. The PGE$_1$ was alprostadil. Considering the response obtained with the two compounds individually, the theoretical concentrations required to achieve a specified level of relaxation (i.e., 10%, 20%, 40%, 60% and 70% relaxation) was calculated assuming an additive effect (open circles). The experimental values obtained from FIG. 2 are denoted by closed circles. In the y axis, the concentration of PGE$_1$ plus 100 fold GS—NO ranges from 0.01 nM to 1000 nM. P<0.05 by ANOVA analysis for the theoretical curve when compared to the experimental curve.

FIG. 4 shows the theoretical relaxation curve calculated assuming an additive effect between $PGE_1$ and GS—NO and the experimental curve obtained with the combination of $PGE_1$ and GS—NO. As can be seen from FIG. 4, the combination of $PGE_1$ and GS—NO was significantly more potent than expected (if only an additive effect was assumed), and shows a statistically significant reduction of the concentrations required to obtain a specified relaxation compared to the calculated additive theoretical curve. This results suggests that there is an unexpected synergism in the relaxation of the human corpus cavernosum induced by the combination of $PGE_1$ and GS—NO.

Example 8

(2S,3S)-2,3,4-Tris(nitroxy)butyl 7-[5-((1E)(3S)-3-hydroxyoct-1-enyl)(1R, 4R,5R)-4-hydroxy-2-oxocyclopentyl]heptanoate 8a. (4S,5S)-4,5-Bis(Hydroxymethyl)-2,2-dimethyl-1,3-dioxolane This material was prepared according to the literature (Bystroem, S.; Hoegberg, H.-E.; Norin, T. *Tetrahedron* 37, 2249–2254 (1981)).

8b. (4S,5S)-5-Hydroxymethyl-4-[4,4-dimethyl-3,3-diphenyl-2-oxa-3-sila]pentyl-2,2-dimethyl-1,3-dioxolane Triethylamine (9.8 g, 9.7 mmol, 13.6 mL) and 4-dimethylaminopyridine (5% mol) were added to the solution of the product of Example 8a (15.8 g, 9.7 mmol) in dry methylene chloride (200 mL). Tert-butyldiphenylchlorosilane (10.7 g, 3.9 mmol 0.4 eq, 10.1 mL) was added to the resulting solution at ambient temperature over a period of 5 minutes.

After the addition was complete, the reaction mixture was stirred at ambient temperature overnight (16 hours). The reaction mixture was poured into a separatory funnel and diluted with methylene chloride (200 mL). The organic layer was first washed with water (200 mL), followed by copper (II) sulfate (3×100 mL, saturated aqueous solution) or until the brilliant blue color of the copper sulfate solution was maintained. The organic layer was dried over sodium sulfate and then concentrated in vacuo to give a faint greenish-yellow oil. This oil was chromatographed on silica gel (400 g), eluted with 3:7 ethyl acetate/hexanes. Concentration of the appropriate fractions gave 10.7 g of title compound as a very viscous pale yellow oil. $^1$H NMR (300 MHz, CDCl$_3$) δ 7.67 (m, 4H), 7.42 (m, 6H), 4.08 (m, 1H), 3.97 (m, 1H), 3.78 (AB part of ABX, 2H, $J_{AB}$=10.7 Hz, $J_{AX}$=7.4 Hz, $J_{BX}$=3.6 Hz, $\Delta v_{AB}$=5.5 Hz), 3.73 (AB part of ABX, 2H, $J_{AB}$=11.8 Hz, $J_{AX}$=4.6 Hz, $J_{BX}$=3.3 Hz, $\Delta v_{AB}$=3.9 Hz), 1.41 (s, 3H), 1.39 (s, 3H), 1.06 (s, 9H).

8c. (2S,3S)-7,7-Dimethyl-5-oxa-6-silaoctan-1,2,3-triol

The product of Example 8b (500 mg, 1.25 mmol) was dissolved in acetonitrile (10 mL) at ambient temperature. Water (0.5 mL, 20 eq) was added followed by PdCl$_2$(CH$_3$CN)$_2$ (10% mol) resulting in a yellowish-orange solution (the catalyst went into solution after about 5–10 minutes). The reaction mixture was stirred at ambient temperature for 6 days. Concentration of the solvent in vacuo gave a dark yellow oil which was preadsorbed on silica gel (1 g). The resulting oil was purified by flash chromatography on silica gel (20 g), eluted with 1:1 ethyl acetate/hexanes (250 mL) followed by ethyl acetate (250 mL). Concentration of the appropriate fractions gave 254 mg of the title compound as a very viscous yellow oil. $^1$H NMR (300 MHz, CDCl$_3$) δ 7.65 (m, 4H), 7.41 (m, 6H), 3.75 (bs, 4H), 3.69 (bs, 4H), 3.0 (vbs, 3H), 1.06 (s, 9H); MS (EI) 378 (M$^+$+18).

8d. (2S,3S)-7,7-Dimethyl-1,2,3-tris(nitrooxy)-5-oxa-6-silaoctane

The product of Example 8c (710 mg, 1.97 mmol) was taken up in methylene chloride (10 mL). Fuming nitric acid (745 mg, 11.8 mmol, 6 eq, 0.53 mL of 90% fuming nitric acid) and acetic anhydride (2.6 mL, 1:5 v/v nitric acid/acetic anhydride) were premixed (exothermic) and then added to the methylene chloride solution at ambient temperature. The resulting yellow solution was stirred at ambient temperature for 20 minutes. TLC indicated the reaction was complete. The reaction mixture was diluted with methylene chloride (50 mL) and then washed with half saturated NaHCO$_3$ solution (2×10 mL). The organic layer was dried over sodium sulfate and then concentrated in vacuo. Final drying under full vacuum to constant weight gave 884 mg (90.6%) of the title compound as a faint orange oil. The compound was used for the next reaction without any further purification. $^1$H NMR (300 MHz, CDCl$_3$) δ 7.61 (m, 4H), 7.44 (m, 6H), 5.72 (m, 1H), 5.24 (m, 1H), 4.75 (AB part of ABX, 2H, $J_{AB}$=13.1 Hz, $J_{AX}$=6.4 Hz, $J_{BX}$=3.4 Hz, $\Delta v_{AB}$=4.9 Hz), 3.89 (bd, 2H, J=4.5 Hz) 1.07 (s, 9H).

8e. (2S,3S)-2,3,4-Tris(nitrooxy)butan-1-ol

The product of Example 8d (884 mg, 1.78 mmol) was dissolved in dry THF (15 mL). Tetra-butylammonium fluoride (2.0 mmol, 2 mL of a 1M solution in THF, 1.1 eq) was added resulting in a brown solution. The reaction mixture was stirred at ambient temperature for 1.5 hours. TLC (3:7 ethyl acetate/hexanes) indicated that the reaction was complete. Silica gel (1.5 g) was added to the reaction mixture and the solvent was removed in vacuo. The preadsorbed material was then flash chromatographed on a silica gel column (20 g), eluted with 1:9 ethyl acetate/hexanes (250 mL) followed by 1:1 ethyl acetate/hexanes (250 mL). Concentration of the appropriate fractions gave 274 mg of the title compound as a very pale yellow oil (60%). $^1$H NMR (300 MHz, CDCl$_3$) δ 5.66 (m, 1H), 5.34 (m, 1H), 4.82 (AB part of ABX, 2H, $J_{AB}$=13.2 Hz, $J_{AX}$=6.0 Hz, $J_{BX}$=3.3 Hz, $\Delta v_{AB}$=4.7 Hz), 3.98 (AB part of ABX, 2H, $J_{AB}$=12.7 Hz, $J_{AX}$=4.6 Hz, $J_{BX}$=4.4 Hz, $\Delta v_{AB}$=4.4 Hz), 2.28 (bs, 1H); $^{13}$C NMR (75.5 MHz, CDCl$_3$) δ 78.72, 75.36, 68.58, 59.71; MS (EI, 70 eV) 256 (M−H).

8f. (2S,3S)-2,3,4-Tris(nitrooxy)butyl 7-[5-((1E)(3S)-3-hydroxyoct-1-enyl)(1R,4R,5R)-4-hydroxy-2-oxocyclopentyl]heptanoate The product of example 8e (250 mg, 0.97 mmol, 1.2 eq) and 7-[5-((1E)(3S)-3-hydroxyoct-1-enyl)(1R,4R,5R)-4-(hydroxy-2-oxocyclopentyl]heptanoic acid (287 mg, 0.81 mmol) were dissolved in dry THF (10 mL) in a dry round-bottomed flask. The resulting pale yellow solution was cooled to 0° C. A catalytic amount of DMAP was added followed immediately by the addition of EDAC.HCl (171 mg, 0.89 mmol, 1.1 eq). The reaction mixture was stirred at 0° C. for 1 hour and then allowed to slowly warm to ambient temperature. Stirring was continued at ambient temperature for 2 days. TLC (ethyl acetate) indicated that the reaction was complete. The reaction mixture was diluted with ethyl acetate and washed with water (2×10 mL). The organic layer was dried over sodium sulfate and concentrated in vacuo to afford a pale yellow oil. The crude product was preadsorbed onto silica gel (1 g) and then flash chromatographed on silica gel (15 g), eluted with 1:1 ethyl acetate/hexanes (250 mL) followed by ethyl acetate (250 mL). Concentration of the appropriate fractions gave 415 mg of the title compound as a viscous, very pale yellow oil (86.4%). $^1$H NMR (300 MHz, CDCl$_3$) δ 5.64 (dd, 1H, J=15.2, 7.3 Hz), 5.54 (m, 3H), 4.77 (AB part of ABX, 2H, $J_{AB}$=13.1 Hz, $J_{AX}$=6.4 Hz, $J_{BX}$=3.6 Hz, $\Delta v_{AB}$=5.0 Hz), 4.40 (AB part of ABX, 2H, $J_{AB}$=12.7 Hz, $J_{AX}$=5.2 Hz, $J_{BX}$=4.2 Hz, $\Delta v_{AB}$=4.7 Hz), 4.11 (m, 3H), 2.45 (AB part of ABX, 2H, $J_{AB}$=18.4 Hz, $J_{AX}$=10.0 Hz, $J_{BX}$=7.5 Hz, $\Delta v_{AB}$=8.7 Hz), 2.33 (t, 2H, J=7.5 Hz), 2.32 (m, 1H), 1.98 (m, 1H), 1.70–1.20 (m, 19H), 0.88 (t, 3H, J=6.6 Hz); $^{13}$C NMR (75.5 MHz, CDCl$_3$) δ 214.78, 172.79, 136.67, 132.12, 76.11, 74.97, 73.09, 71.75, 68.18, 60.04, 54.77, 54.38, 45.78, 37.18, 33.62, 31.59, 29.15, 28.59, 27.50, 26.45, 25.08, 24.47, 22.55, 13.94; MS (EI, 70 eV) 611 (M+NH$_4$)$^+$.

Example 9

(2S)-2,3-Bis(nitroxy)propyl 7-[5-((1E)(3S)-3-hydroxyoct-1-enyl) (1R,4R,5R)-4-(hydroxy-2-oxocyclopentyl]heptanoate 2,3-bis(nitroxy)propan-1-ol (145 mg, 0.80 mmol, 1.2 eq) and 7-[5-((1E)(3S)-3-hydroxyoct-1-enyl)(1R,4R,5R)-4-(hydroxy-2-oxocyclopentyl)heptanoic acid (234 mg, 0.66 mmol) were dissolved in dry THF (6 mL) in a dry round-bottomed flask. The clear solution was cooled to 0° C. A catalytic amount of DMAP was added followed immediately by EDAC.HCl (146 mg, 0.76 mmol, 1.15 eq). The reaction mixture was stirred at 0° C. for 1 hour and then allowed to warm to ambient temperature. The reaction was stirred at ambient temperature for 2 days. TLC (ethyl acetate) indicated that the reaction was complete. The reaction mixture was diluted with ethyl acetate and then washed with water. The organic layer was dried over sodium sulfate, filtered and then concentrated in vacuo to afford a yellow oil. The oil was preadsorbed onto silica gel (1 g) and then applied to a flash column, eluted with 1:1 ethyl acetate/hexanes (250 mL) followed by ethyl acetate (250 mL). Concentration of the appropriate fractions gave 287 mg of the title compound as an extremely viscous clear oil (83.6%). $^1$H NMR (300 MHz, CDCl$_3$) δ 5.62 (dd, 1H, J=15.5, 7.4 Hz), 5.47 (dd, 1H, J=15.5, 8.4 Hz), 5.44 (m, 1H), 4.69 (AB part of ABX, 2H, $J_{AB}$=12.9 Hz, $J_{AX}$=6.8 Hz, $J_{BX}$=3.8 Hz, $\Delta v_{AB}$=5.3 Hz), 4.34 (AB part of ABX, 2H, $J_{AB}$=12.6 Hz, $J_{AX}$=5.6 Hz, $J_{BX}$=4.1 Hz, $\Delta v_{AB}$=4.9 Hz), 4.05 (m, 3H), 2.45 (AB part of ABX, 2H, $J_{AB}$=18.4 Hz, $J_{AX}$=10.0 Hz, $J_{BX}$=7.5 Hz, $\Delta v_{AB}$=8.8 Hz), 2.31 (t, 2H, J=7.5 Hz), 1.96 (m, 1H), 1.70–1.15 (m, 20H), 0.86 (t, 3H, J=6.5 Hz); $^{13}$C NMR (75.5 MHz, CDCl$_3$) δ 214.77, 172.90, 136.63, 132.27, 76.21, 73.12, 71.70, 68.61, 60.36, 54.81, 54.38, 45.76, 37.13, 33.65, 31.58, 29.21, 28.64, 27.54, 26.50, 25.07, 24.53, 22.53, 13.94; MS (70 eV, EI) 536 (M+NH$_4$)$^+$.

Example 10

(2S)-2,3-Bis(nitroxy)propyl 7-[5-((1E)(3S)-3-(nitrooxyoct-1-enyl) (1R,4R,5R)-4-(nitrooxy)-2-oxocyclopentyl]heptanoate The product of Example 9 (232 mg, 0.48 mmole) was dissolved in dry methylene chloride (4 mL). The solution was cooled to 0° C. Fuming nitric acid (113 mg, 1.79 mmole, 4eq, 0.08 mL) and acetic anhydride (0.4 mL) were premixed neat (very exothermic reaction) and the pale yellow solution was then added dropwise to the methylene chloride solution. The faint yellow reaction mixture was stirred at 0° C. for 1 minute. TLC (1:1 EtOAc/hexanes) indicated that the reaction was complete. The reaction mixture was diluted with methylene chloride (10 mL) and the organic layer was washed with 20% aqueous NaHCO$_3$ (2×5 mL). The combined aqueous layers were then back extracted with methylene chloride (5 mL) and the combined organic layers were dried over sodium sulfate. The solvent was concentrated in vacuo and residual solvent was removed under vacuum producing 270 mg of the title compound as a very viscous pale yellow oil (99%): $^1$H NMR (300 MHz, CDCl$_3$) δ 5.76 (dd, 1H, J=15.5, 8.2 Hz), 5.60 (dd, 1H, J=15.5, 7.0 Hz), 5.42 (m, 1H), 5.21 (m, 2H), 4.65 (AB part of ABX, 2H, $J_{AB}$=12.9 Hz, $J_{AX}$=6.8 Hz, $J_{BX}$=3.9 Hz, $\Delta v_{AB}$=5.3 Hz), 4.30 (AB part of ABX, 2H, $J_{AB}$=12.6 Hz, $J_{AX}$=5.7 Hz, $J_{BX}$=4.0 Hz, $\Delta v_{AB}$=4.8 Hz), 2.63 (dt, 1H, J=11.4, 8.6 Hz), 2.55 (AB part of ABX, 2H, $J_{AB}$=18.7 Hz, $J_{AX}$=8.0 Hz, $J_{BX}$=7.6 Hz, $\Delta v_{AB}$=7.7 Hz), 2.28 (t, 2H, J=7.5 Hz), 2.10, (m, 1H), 1.80–1.10 (m, 18H), 0.82 (t, 3H, J=6.6 Hz); $^{13}$C NMR (75.5 MHz, CDCl$_3$) δ 211.06, 173.23, 133.60, 130.66, 83.67, 81.51, 76.67, 69.05, 60.76, 54.08, 49.01, 42.89, 34.02, 32.63, 31.63, 29.49, 28.95, 27.80, 26.74, 25.00, 24.88, 22.74, 14.23; MS (70 eV, EI) 626 (M+NH$_4$)$^+$.

Example 11

3-Nitrooxy-2,2-bis(nitrooxymethyl)propyl 7-[5-((1E)(3S)-3-hydroxyoct-1-enyl) (1R,4R,5R)-4-hydroxy-2-oxocyclopentyl]heptanoate 11a. 2,2-Bis(hydroxymethyl)-6,6-dimethyl-5,5-diphenyl-4-oxa-5-silaheptan-1-ol 2,2-bis(hydroxymethyl)propane-1,3-diol (10.55 g, 77 mmole) was taken up in dry pyridine (100 mL). Tert-butyldiphenylsilyl chloride (4.26 g, 15 mmole, 0.2 eq) was then added dropwise over 10 minutes to the pyridine solution at ambient temperature. The reaction mixture was stirred at ambient temperature for 24 hours. TLC (EtOAc) indicated that the reaction was complete. The reaction was diluted with EtOAc (250 mL), washed with 10% HCl (3×200 mL). The organic layer was dried over sodium sulfate and then concentrated in vacuo to afford a thick pale yellow oil. Column chromatography on silica gel (200 g), eluted with EtOAC followed by concentration of the appropriate fractions gave 5.01 g of the title compound as a clear colorless oil which solidified very slowly upon standing (86%). $^1$H NMR (300 MHz, CDCl$_3$) δ 7.65 (m, 4H), 7.42 (m, 6H), 3.74 (s, 6H), 3.66 (s, 2H), 1.08 (s, 9H); MS (70 eV, EI) 392 (M+NH$_4$)$^+$.

11b. 2,2-Dimethyl-1-nitrooxy-2,2-bis(nitrooxymethyl)-4-oxa-5,5-diphenyl-5-silaheptane The product of Example 11a (332 mg, 0.89 mmole) was dissolved in dry methylene chloride (4 mL). Fuming nitric acid (335 mg, 5.32 mmole, 6 eq, 0.24 mL of the 90% nitric acid) and acetic anhydride (1.20 mL) were premixed (exothermic) and then the pale yellow solution was added dropwise to the methylene chloride solution at ambient temperature. The reaction mixture was stirred at ambient temperature for 30 minutes. TLC (7:3 EtOAc/hexanes) indicated that the reaction was complete. The reaction mixture was diluted with methylene chloride (20 mL) and then washed with sodium bicarbonate (2×10 mL, saturated aq.). The organic layer was then dried over sodium sulfate and the solvent was concentrated in vacuo to give 400 mg of the title compound as a pale yellow oil which was used as is for the next reaction (88.6%). $^1$H NMR (300 MHz, CDCl$_3$) δ 7.53 (m, 4H), 7.35 (m, 6H), 4.40 (s, 6H), 3.64 (s, 2H), 0.99 (s, 9H); MS (70 eV, EI) 527 (M+NH$_4$)$^+$.

11c. 3-Nitrooxy-2,2-bis(nitrooxymethyl)propan-1-ol

The product of Example 11b (400 mg, 0.79 mmole) was dissolved in THF (5 mL). Tetrabutyl-n-butylammonium fluoride (1.2 eq, 0.94 mmole, 0.94 mL of the 1M solution in THF) was added at ambient temperature to produce a dark brown solution. The reaction mixture was stirred at ambient temperature for 1.5 hours. TLC (1:9 EtOAc/hexanes) indicated that the reaction was complete. The reaction mixture was passed through a short pad of silica gel, eluted with 1:1 EtOAc/hexanes. Concentration of the solvent in vacuo gave a pale yellow oil. This oil was chromatographed on analytical TLC plates (8 10×20 cm 0.25 mm), eluted first with 1:9 EtOAc/hexanes (1×) followed by 1:3 EtOAc/hexanes (2×). Extraction of the desired band into EtOAc followed by concentration of the solvent in vacuo gave 150 mg of the title compound as a pale yellow oil which solidifies very slowly upon standing (71%). $^1$H NMR (300 MHz, CDCl$_3$) δ 4.51 (s, 6H), 3.71 (s, 2H); MS (70 eV, EI) 289 (M+NH$_4$)$^+$.

11d. 3-Nitrooxy-2,2-bis(nitrooxymethyl)propyl 7-[5-((1E)(3S)-3-hydroxyoct-1-enyl)(1R,4R,5R)-4-hydroxy-2-oxocyclopentyl]heptanoate The product of Example 11c (132 mg, 0.487 mmole, 1.5 eq) dissolved in dry THF (1 mL) was added to 7-[5-((1E) (3S)-3-hydroxyoct-1-enyl)(1R,4R,5R)-4-(hydroxy-2-oxocyclopentyl]heptanoic acid (115 mg, 0.325 mmole) dissolved in dry THF (4 mL) under argon in an oven-dried round-bottomed flask. The resulting pale yellow clear solution was cooled to 0° C. A few crystals of DMAP were added at 0° C. followed immediately by the addition of EDAC.HCl (94 mg, 0.487 mmole, 1.5 eq). The reaction mixture was stirred at 0° C. for 1 hour and then slowly warmed to ambient temperature overnight. Stirring was continued at ambient temperature for 2 days. TLC (EtOAc) indicated the reaction was complete. The reaction mixture was diluted with EtOAc and washed with water (2×10 mL). The organic layer was dried over sodium sulfate, the solvent was concentrated in vacuo and then preadsorbed onto silica gel (1 g). The mixture was then flash chromatographed on silica gel (15 g), eluted first with 1:1 EtOAC/hexanes (250 ml) followed by EtOAc (250 mL). Concentration of the appropriate fractions in vacuo and removal of residual solvent on vacuum gave 163 mg of the title compound as a colorless viscous oil (83%). $^1$H NMR (300 MHz, CDCl$_3$) δ 5.55 (dd, 1H, J=15.2, 7.6 Hz), 5.43 (dd, 1H, J=15.2, 8.6 Hz), 4.51 (s, 6H), 4.13 (s, 2H), 3.92 (m, 2H), 3.71 (bs, 2H), 2.39 (AB part of ABX, 2H, J$_{AB}$=18.4 Hz, J$_{AX}$=9.8 Hz, J$_{BX}$=7.5 Hz, Δv=8.7 Hz), 2.27 (t, 2H, J=7.6 Hz), 2.23 (m, 1H), 1.89 (m, 1H), 1.65–1.15 (m, 18H), 0.81 (t, 3H, J=6.5 Hz); $^{13}$C NMR (75.5 MHz, CDCl$_3$) δ 215.36, 173.01, 136.94, 132.84, 73.55, 71.95, 69.72, 61.79, 55.16, 54.69, 46.09, 42.26, 37.34, 34.01, 31.91, 29.51, 28.96, 27.83, 26.83, 25.40, 24.86, 22.88, 14.26; MS (70 eV, EI) 625 (M+NH$_4$)$^+$.

Example 12

3-Nitrooxy-2,2-bis[(nitrooxy)methyl]propyl 7-[5-[(1E)(3S)-3-(nitrooxyoct-1-enyl) (1R,4R,5R)-4-nitrooxy-2-oxocyclopentyl]heptanoate Fuming nitric acid (72 mg, 1.14 mmole, 0.05 mL of the 90% solution) and acetic anhydride (0.25 mL) were premixed (exothermic). The resulting yellow solution was added dropwise to the product of Example 11 in dry methylene chloride (4 mL) under argon at 0° C., resulting in a pale yellow solution. Stirring was continued at 0° C. for 1 minute. TLC (1:1 EtOAc/hexanes) indicated that the reaction was complete. The reaction mixture was diluted with methylene chloride and washed with sodium bicarbonate (2×5 mL, 20% aqueous). The combined aqueous layers were back-extracted with methylene chloride (5 mL). The combined organic layers were dried over sodium sulfate and then the solvent was removed in vacuo followed by final removal of residual solvent under vacuum to give 197 mg of the title compound as a pale yellow viscous oil (99%). $^1$H NMR (300 MHz, CDCl$_3$) δ 5.76 (dd, 1H, J=15.5, 8.1 Hz), 5.61 (dd, 1H, J=15.5, 7.0 Hz), 5.21 (m, 2H), 4.51 (s, 6H), 4.14 (s, 2H), 2.64 (dt, 1H, J=11.4, 8.5 Hz), 2.61 (AB part of ABX, 2H, J$_{AB}$=18.6 Hz, J$_{AX}$=8.0 Hz, J$_{BX}$=7.7 Hz, Δv$_{AB}$=7.8 Hz), 2.28 (t, 2H, J=7.6 Hz), 2.08 (m, 1H), 1.75–1.10 (m, 18H), 0.82 (t, 3H, J=6.4 Hz); $^{13}$C NMR (75.5 MHz, CDCl$_3$) δ 211.10, 172.96, 133.56, 130.62, 83.69, 81.53, 69.75, 61.82, 54.03, 48.96, 42.86, 42.35, 34.05, 32.60, 31.61, 29.43, 28.94, 27.75, 26.68, 24.98, 24.86, 22.73, 14.22; MS (70 eV, EI) 715 (M+NH$_4$)$^+$.

Example 13

Methyl 7-[5-((1E)(3S)-3-nitroxyoct-1-enyl)(1R,4R,5R)-4-nitrooxy-2-oxocyclopentyl]heptanoate 13a. Methyl 7-[5-((1E)(3S)-3-hydroxyoct-1-enyl) (1R,4R,5R)-4-hydroxy-2-oxocyclopentyl]heptanoate 7-[5-((1E)(3S)-3-hydroxyoct-1-enyl)(1R,4R,5R)-4-(hydroxy-2-oxocyclopentyl)heptanoic acid (311 mg, 0.877 mmol) was slurried in diethyl ether (10 mL) in a 50 mL erlenmeyer flask and cooled to 0° C. In a separate 50 mL erlenmeyer flask, N-methyl-N-nitrosourea (271 mg, 2.63 mmol, 3 eq) was added to a 1:1 mix of water/diethyl ether (20 mL) and cooled to 0° C. KOH was added to the N-methyl-N-nitrosourea mix at 0° C., generating diazomethane as evidenced by the formation of a yellow color in the diethyl ether layer. After 5 minutes, the yellow ethereal diazomethane solution was slowly added to the prostaglandin solution via a flame polished pipette slowly resulting in the dissolution of the solid material. Once the prostaglandin had gone into solution and a yellow color was maintained in the reaction mixture, addition of the ethereal diazomethane was stopped and both mixtures were allowed to slowly warm to ambient temperature and left until all the yellow color had disappeared. The prostaglandin reaction mixture was dried over sodium sulfate and then the solvent was concentrated in vacuo to give the title compound as a clear colorless oil (99.5%): $^1$H NMR (300 MHz, CDCl$_3$) δ 5.63 (dd, 1H, J=15.3, 6.8 Hz), 5.49 (dd, 1H, J=15.3, 8.5 Hz), 4.02 (m, 2H), 3.59 (s, 3H), 2.42 (AB part of ABX, 2H, J$_{AB}$=18.4 Hz, J$_{AX}$=9.8 Hz, J$_{BX}$=6.6 Hz, Δv$_{AB}$=8.2 Hz), 2.29 (dt, 1H, J=12.0, 8.6 Hz), 2.22 (t, 2H, J=7.4 Hz), 1.94 (m, 1H), 1.80–1.15 (m, 18H), 0.82 (t, 3H, J=6.5 Hz).

13b. Methyl 7-[5-((1E)(3S)-3-nitroxyoct-1-enyl) (1R,4R,5R)-4-nitrooxy-2-oxocyclopentyl]heptanoate Fuming nitric acid (189 mg, 3.00 mmole, 4 eq, 0.14 mL of the 90% solution) and acetic anhydride (0.67 mL) were premixed (exothermic) and the resulting yellow solution was added dropwise to the product of Example 13a (276 mg, 0.75 mmole) in dry methylene chloride (5 mL) under argon at 0° C. to give a pale yellow solution. Stirring was continued at 0° C. for 1 minute. TLC (1:1 EtOAc/hexanes) indicated that the reaction was complete. The reaction mixture was diluted with methylene chloride and the organic layer was washed with 20% aqueous sodium bicarbonate (2×5 mL). The combined aqueous layers were back-extracted with methylene chloride (5 mL). The combined organic layers were dried over sodium sulfate and then the solvent was concentrated in vacuo followed by the final removal of residual solvent under vacuum to gave 337 mg of the title compound as a pale yellow viscous oil (98%): $^1$H NMR (300 MHz, CDCl$_3$) δ 5.76 (dd, 1H, J=15.5, 8.3 Hz), 5.60 (dd, 1H, J=15.5, 7.1 Hz), 5.21 (m, 2H), 3.59 (s, 3H), 2.64 (dt, 1H, J=11.5, 8.5 Hz), 2.62 (AB part of ABX, 2H, J$_{AB}$=18.9 Hz, J$_{AX}$=8.1 Hz, J$_{BX}$=7.6 Hz, Δv$_{AB}$=7.9 Hz), 2.23 (t, 2H, J=7.3 Hz), 2.10 (m, 1H), 1.70–1.15 (m, 18H), 0.82 (t, 3H, J=6.7 Hz); $^{13}$C NMR (75.5 MHz, CDCl$_3$) δ 210.65, 174.14, 133.34, 130.19, 83.24, 81.03, 53.65, 51.38, 48.59, 42.46, 33.83, 32.18, 31.18, 29.13, 28.65, 27.40, 26.33, 24.66, 24.54, 22.23, 13.78: MS (70 eV, EI) 476 (M+NH$_4$)$^+$.

Example 14

2-[2-(Nitrosothio)adamantan-2-yl]ethyl 7-[5-((1E) (3S)-3-hydroxyoct-1-enyl)(1R,4R,5R)-4-hydroxy-2-oxocyclopentyl]heptanoate 14a. Adamantane-2-thione Adamantan-2-one (48.46 g, 322.6 mmol) in pyridine (300 mL) was heated to 90° C. and phosphorous pentasulfide (17.84 g, 40.13 mmol) was added. The reaction was maintained at 90° C. for two hours and at room temperature overnight during which time a precipitate formed. The pyridine solution was decanted and concentrated to dryness. The residual semisolid was treated with hexane (400 mL) to give an orange solution with a light brown suspension. The suspension was removed by filtration. The filtrate was concentrated to dryness and dried to vacuum to give an orange solid (50.36 g). This crude product was purified by filtration through a pad of silica gel (hexane). $^1$H NMR (CDCl$_3$, 300 MHz): 83.43 (s, 2H), 2.1–1.9 (m, 12H); $^{13}$C NMR (75 MHz, CDCl$_3$): δ 222.4, 57.5, 41.1, 36.5, 27.4.

14b. tert-Butyl 2-(2-sulfanyladamantan-2-yl)acetate

To t-butyl acetate (25 mL, 21.6 g, 186 mmol) in dry THF (400 mL) at −78° C. was added lithium diisopropylamide monotetrahydrofuran (1.5 M solution in cyclohexane, 100 mL, 150 mmol) under nitrogen and the reaction mixture was stirred at −78° C. for 40 minutes. The product of Example 14a (21.88 g, 131.57 mmol) in THF (400 mL) was added. The cold bath was removed and the reaction was stirred at room temperature for two hours. The reaction was diluted with methylene chloride and 2 M HCl (75 mL) was added. The organic phase was separated, washed with brine (4×40 mL), dried (MgSO$_4$), filtered, and concentrated. The crude product was purified by filtration through a pad of silica gel (5% EtOAc/95% hexane) to give the title compound (34.67 g, 122.7 mmol, 93%). R$_f$=0.48 (EtOAc/hexane 1:19); $^1$H NMR (CDCl$_3$, 300 MHz): δ 2.87 (s, 2H), 2,47 (d, I=11.5, 2H), 2.38 (s, 1H), 2.11 (d, J=11.9, 2H), 1.98 (s, 2H), 1.96 (m, 2H), 1.84–1.62 96 (m, 6H), 1.47 (s, 9H); $^{13}$C NMR (75 MHz, CDCl$_3$): δ 170.8, 80.7, 54.1, 47.3, 39.0, 38.2, 37.2, 36.6, 34.0, 33.3, 28.2, 27.5, 26.9. APIMS (1S, NH$_4$OAc) m/e 283 (MH$^+$); Anal. Calcd for C$_{16}$H$_{26}$O$_2$S (282.44): C, 68.04; H, 9.28 Found: C, 68.14; H, 9.30.

14c. 2-(2-Sulfanyladamantan-2-yl)ethan-1-ol

To a 0° C. cooled solution of Example 14b (4.1 g, 24.1 mmol) in anhydrous dichloromethane (40 mL) lithium aluminum hydride (1 M solution in THF) (40 mL) was added dropwise over a period of 20 minutes. The reaction mixture was stirred at 0° C. for further 15 minutes and then at room temperature for 30 minutes. The excess LiAlH$_4$ was destroyed by the addition of ethyl acetate. The reaction mixture was then poured over ice cold water, acidified with 1 N HCl and extracted with dichloromethane (2×200 mL). The combined extracts were washed with brine (1×75 mL), dried over sodium sulfate, filtered and solvent evaporated at reduced pressure to give the title compound (3.1 g), mp 68–70° C.; $^1$H NMR (CDCl$_3$): δ 1.16–1.9 (m, 11H), 2.1 (m, 2H), 2.22 (t, J=6.9 Hz, 3H), 2.43 (m, 2H), 3.93 (t, J=6.9 Hz, 2H); $^{13}$C NMR (CDCl$_3$): δ 26.8, 27.7, 33.2, 33.9, 38.2, 39.1, 43.4, 55.8, 59.4; LRMS (APIMS) (m/z) 230 (M+18) (M+NH$_4$).

14d. 2-[2-(Nitrosothio)adamantan-2-yl]ethan-1-ol

To a 0° C. cooled solution of Example 14c (1.06 g, 5 mmol) in anhydrous dichloromethane (40 mL) was added t-butyl nitrite (7.5 mmol, 890 μL). The reaction mixture was stirred at 0° C. for 30 minutes and then at room temperature for 30 minutes. The solvent was removed at reduced pressure and product was recrystallized from ethyl ether/hexane to give 1.2 g (80% yield) of the title compound as a green crystalline solid, mp 77–79° C.; $^1$H NMR (CDCl$_3$): δ 1.7–1.74 (m, 2H), 1.83–1.93 (m, 5H), 2.06 (m, 3H), 2.42–2.53 (m, 4H), 2.99 (t, J=7.3 Hz, 2H), 3.83 (t, J=7.6 Hz, 2H); $^{13}$C NMR (CDCl$_3$): δ 27.3, 27.4, 33.2, 33.9, 35.6, 38.97, 39.96, 59.1, 68.2; LRMS (APIMS) (m/z) 259 (M+18) (M+NH$_4$).

14e. 2-[2-(Nitrosothio)adamantan-2-yl]ethyl 7-[5-((1E)(3S)-3-hydroxyoct-1-enyl)(1R,4R,5R)-4-hydroxy-2-oxocyclopentyl]heptanoate 7-[5-((1E)(3S)-3-hydroxyoct-1-enyl)(1R,4R,5R)-4-(hydroxy-2-oxocyclopentyl)heptanoic acid (36.2 mg, 0.102 mmol) was dissolved in 1.5 mL of dry tetrahydrofuran (THF) and cooled to 0° C. under argon. DMAP (catalytic) and EDAC.HCl (30 mg, 0.153 mmol, 1.5 eq) were then added. This was followed immediately by the addition of Example 14d (44 mg, 0.182 mmol, 1.8 eq) dissolved in 1 mL of dry THF. The reaction mixture was protected from light by wrapping the reaction flask in aluminum foil. The reaction mixture was stirred at 0° C. for 1 hour and then gradually warmed to ambient temperature. The reaction mixture was stirred at ambient temperature for 2 days during which time the green color of the nitrosothiol was maintained. TLC (EtOAc) indicated that the reaction was complete. The reaction mixture was then directly applied to two 10×20 cm 0.25 mm thick TLC plates and eluted once with 1:1 EtOAc/hexanes. Extraction of the most polar green band into EtOAc, filtration and concentration of the solvent in vacuo gave the title compound as a thick green oil (41 mg, 69.5% yield): $^1$H NMR (300 MHz, CDCl$_3$) δ 5.58 (dd, 1H, J=15.3, 6.8 Hz), 5.45 (dd, 1H, J=15.3, 8.4 Hz), 4.14 (t, 2H, J=7.3 Hz), 3.98 (m, 2H), 2.95 (t, 2H, J=7.3 Hz), 2.70–1.05 (m, 38H), 0.79 (t, 3H, J=6.5 Hz).

Example 15

[{1-[(4-methylphenyl)sulfonyl]-4-(nitrosothiol)-4-piperidyl}methyl 7-[5-((1E)(3S)-3-hydroxyoct-1-enyl)(1R,4R,5R)-4-hydroxy-2-oxocyclopentyl] heptanoate 15a. 1-[(4-methylphenyl)sulfonyl]piperidin-4-one para-Toluenesulfonyl chloride (13.8 g, 72.2 mmol) was added to a suspension of 4-piperidone (10.1 g, 65.7 mmol) and triethylamine (7.30 g, 72.2 mmol) in CH$_2$Cl$_2$ (100 ml). After stirring at room temperature for 2 hours DMF (50 ml) was added to the reaction mixture and the stirring was continued overnight. The reaction mixture was concentrated in vacuo and saturated aqueous sodium bicarbonate was added to the residue. The resulting precipitate which formed was collected by suction filtration. The precipitate was washed with water followed by hexane and then dried under high vacuum to afford a white solid (9.4 g) which was used without further purification. $^1$H NMR (300 MHz, CDCl$_3$) δ 7.69 (d, 2H, J=8.1 Hz), 7.34 (d, 2H, J=8.1 Hz) 3.39 (m, 4H), 2.55 (m, 4H), 2.44 (s, 3H).

15b. 6-aza-6-[(4-methylphenyl)sulfonyl]-1-thiaspiro [2.5]octane

To a solution of sodium hydride (1.9 5 g, 48.5 mmol) in DMSO (100 ml) was added trimethylsulfoxium iodide (10.7 g, 48.5 mmol) portionwise and the reaction mixture was stirred at room temperature for 30 minutes. The product of Example 15a (9.4 g, 37.3 mmol) in DMSO (20 ml) was added and the reaction mixture was heated to 60° C. for 1 hour. After cooling to room temperature, the reaction mixture was poured into water and the resulting precipitate collected by suction filtration. The precipitate was dissolved in THF (100 ml) and then water (100 ml) was added, yielding a cloudy solution. To this solution was added potassium thiocyanate (10.9 g, 111 mmol) and DMSO (20 ml). The resulting mixture was stirred at room temperature overnight. The reaction mixture was poured into water and the resulting precipitate was collected by suction filtration. The precipitate was washed with water followed by hexane, dried under high vacuum to yield a white solid (6.7 g) which was used without further purification. $^1$H NMR (300 MHz, CDCl$_3$) δ 7.68 (d, 2H, J=8.1 Hz), 7.34 (d, 2H, J=8.1 Hz) 3.72 (m, 2H), 2.68 (m, 2H), 2.45 (s, 3H) 2.35 (m, 2H), 1.57–1.46 (m, 4H).

15c. 4-(hydroxymethyl)-1-[(4-methylphenyl)sulfonyl]piperidine-4-thiol

To a solution of acetic acid (10.6 ml), acetic anhydride (50 ml), and sodium acetate (10.6 g) was added the product of Example 15b (2.0 g, 7.1 mmol). The reaction was stirred at 130° C. overnight. After cooling the reaction mixture to room temperature, water was added and the resulting precipitate was collected by suction filtration and dried under high vacuum. The white solid (1.75 g, 4.5 mmol) was dissolved in THF (10 ml), cooled to 0° C., and lithium aluminium hydride (9.1 ml, 1.0 M/THF) was added. After stirring at 0° C. for one hour, the reaction was quenched by slow addition to 1N HCl. Extraction of the mixture with CH$_2$Cl$_2$ followed by drying the organic phase over sodium sufate and concentration in vacuo gave the crude product which was purified by flash chromatography on silica gel (1:1 EtOAc/hexanes). $^1$H NMR (300 MHz, CDCl$_3$) δ 7.66 (d, 2H, J=8.1 Hz), 7.34 (d, 2H, J=8.1 Hz) 3.63 (m, 2H), 3.48 (m, 2H), 2.80 (m, 2H), 2.45 (s, 3H), 2.08 (m, 1H), 1.83–1.78 (m, 2H), 1.70–1.65 (m, 2H), 2.25 (s, 1H).

15d. 4-(hydroxymethyl)-1-[(4-methylphenyl)sulfonyl]-4-(nitrosothio)piperidine To t-BuONO (610 mg, 5.5 mmol) in CH$_2$Cl$_2$ (10 ml) was added two drops of saturated HCl in ether and then the product of Example 15c (960 mg, 3.6 mmol) in CH$_2$Cl$_2$ (10 ml) was added dropwise over 10 minutes. After stirring for 30 minutes the reaction mixture was concentrated in vacuo and the residue purified by flash chromatography on silica gel (3.:1 EtOAc/hexanes) to afford the title compound. $^1$H NMR (300 MHz, CDCl$_3$) δ 7.62 (d, 2H, J=8.1 Hz), 7.31 (d, 2H, J=8.1 Hz) 3.62 (m, 2H), 3.48 (m, 2H), 2.80 (m, 2H), 2.43 (s, 3H), 2.68–2.41 (m, 8H).

15e. {1-[(4-methylphenyl)sulfonyl]-4-(nitrosothio)-4-piperidyl}methyl 7-[5-((1E)(3S)-3-hydroxyoct-1-enyl)(1R,4R,5R)-4-hydroxy-2-oxocyclopentyl]heptanoate 7-[5-((1E)(3S)-3-hydroxyoct-1-enyl)(1R,4R,5R)-4-hydroxy-2-oxocyclopentyl]heptanoic acid (21.3 mg, 0.060 mmol) was dissolved in 1 ml of dry THF and cooled to 0° C. under argon. DMAP (catalytic) and EDAC.HCl (14 mg, 0.072 mmol, 1.2eq) were then added. This was followed immediately by the addition of the product of Example 15d (25 mg, 0.072 mmol, 1.2eq) dissolved in 0.8 mL of dry THF. The reaction mixture was protected from light by wrapping the reaction flask in aluminum foil. The reaction was stirred at 0° C. for 1 hour and then warmed gradually to ambient temperature. The reaction mixture was stirred at ambient temperature for 2 days during which time the green color of the nitrosothiol was maintained, Thin layer chromatography (TLC, EtOAc)) indicated that the reaction was complete. The reaction mixture was directly applied to two 10×20 cm 0.25 mm thick TLC plates and eluted twice with 1:1 EtOAc/hexanes. Extraction of the more polar green band into EtOAc, filtration and concentration of the solvent in vacuo gave the title compound as a thick green oil (25 mg, 62% yield): $^1$H NMR (300 MHz, CDCl$_3$) δ 7.54 (m, 2H), 7.24 (m, 2H), 5.64 (dd, 1H, J=15.3, 6.6 Hz), 5.59 (dd, 1H, J=15.3, 8.5 Hz), 4.61 (s, 2H), 4.01 (m, S 2H), 3.69 (m, 2H), 2.70–1.90 (m, 12H), 2.36 (s, 3H), 1.75–1.15 (m, 18H), 0.82 (t, 3H, 6.6 Hz); MS (CI (pos)) 689 (M+Na$^+$), (CI(neg)) 665 (M−1)$^−$.

Example 16

2-methyl-2-(nitrosothio)propyl 7-[5-((1E)(3S)-3-hydroxyoct-1-enyl) (1R,4R,5R)-4-hydroxy-2-oxocyclopentyl]heptanoate

16a. 2-methyl-2-sulfanylpropan-1-ol

To 2-methylpropanal (3.53 g, 72 mmol) in carbon tetrachloride (30 ml) was added sulfur monochloride (2 ml, 25 mmol) and the reaction mixture was stirred at 55° C. for 2 hours. After cooling to room temperature, the volatiles were evaporated in vacuo to give 2-[(1,1-dimethyl-2-oxoethyl)disulfanyl]-2-methylpropanal. The disulfide (17.5 g, 85.7 mmol) was dissolved in THF (100 ml) and LiAlH$_4$ (86 ml, 1M/THF) was added slowly. After stirring at room temperature for 1 hour, the mixture was poured onto ice, treated with 3N HCl (150 ml) and then extracted with EtOAc. The organic extracts were dried over sodium sulfate and the volatiles were evaporated to yield 12.8 g (71%) of the title compound as a colorless oil. $^1$H NMR (300 MHz, CDCl$_3$) δ3.44 (s, 2H), 2.25 (brs, 1H), 1.63 (s, 1H), 1.36 (s, 6H); $^{13}$C NMR (CDCl$_3$) 73.3, 46.3, 28.3.

16b. 2-methyl-2-(nitrosothio)propan-1-ol

To a solution of Example 16a (4.4 g, 41.5 mmol) in CH$_2$Cl$_2$ (50 ml) was added t-BuONO (5.5 ml, 41.5 mmol). The reaction mixture was stirred at room temperature for 10 minutes and the volatiles were evaporated in vacuo at 40° C. to give 4.6 g (82%) of the title compound as a dark green oil. $^1$H NMR (300 MHz, CDCl$_3$) δ 4.17 (s, 2H), 1.95 (brs, 1H), 1.90 (s, 6H); $^{13}$C NMR (CDCl$_3$) 70.5, 57.7, 25.1.

16c. 2-methyl-2-(nitrosothio)propyl 7-[5-((1E)(3S)-3-hydroxyoct-1-enyl)(1R,4R,5R)-4-hydroxy-2-oxocyclopentyl]heptanoate 7-[5-((1E)(3S)-3-hydroxyoct-1-enyl)(1R,4R,5R)-4-(hydroxy-2-oxocyclopentyl)heptanoic acid (484 mg, 1.37 mmol) was dissolved in 20 mL of dry THF and cooled to 0° C. under argon. DMAP (catalytic) and EDAC (392 mg, 2.05 mmol, 1.5 eq) were then added. This was followed immediately by the addition of Example 16b (338 mg, 2.5 mmol, 1.8 eq) dissolved in 5 mL of dry THF. The reaction mixture was protected from light by wrapping the reaction flask in aluminum foil. The reaction was stirred at 0° C. for 1 hour and then warmed gradually to ambient temperature. The reaction was stirred at ambient temperature for 1 day during which time the green color of the nitrosothiol was maintained. TLC (EtOAc) indicated that the reaction was complete. The reaction mixture was worked-up by dilution with EtOAc and the organic layer was washed with water (2×20 mL) followed by brine (1×20 mL). The aqueous washings were then back-extracted 2×10 mL with EtOAc. The combined organic layers were then dried over sodium sulfate, filtered and concentrated in vacuo to give a reddish green oil. Pre-adsorption of the oil onto 1.5 g of silica gel followed by flash chromatography on a 20 g column eluting with 250 mL each of 2:3 EtOAc/hexanes and 4:1 EtOAc/hexanes gave fractions containing product. Concentration of the desired fractions in vacuo gave the title compound as a very viscous dark green oil (193 mg, 30% yield): $^1$H NMR (300 MHz, CDCl$_3$) δ 5.72 (dd, 1H, J=15.3, 6.6 Hz), 5.59 (dd, 1H, J=15.3, 8.6 Hz), 4.65 (s, 2H), 4.11 (m, 2H), 2.41 (AB part of ABX, 2H, J$_{AB}$=12.6 Hz, J$_{Ax}$=5.7 Hz, J$_{BX}$=4.0 Hz, Δv$_{AB}$=7.4 Hz), 2.27 (t, 2H, J=7.5 Hz), 2.24 (m, 1H), 1.91 (m, 1H), 1.87 (s, 6H), 1.75–1.15 (m, 18H), 0.83 (t, 3H, 6.6 Hz); $^{13}$C NMR (75.5 MHz, CDCl$_3$) 8214.84, 173.26, 136.55, 132.43, 73.14, 71.61, 70.75, 54.81, 54.34, 45.71, 36.97, 33.93, 31.55, 29.22, 28.69, 27.58, 26.54, 25.83, 25.03, 24.96, 24.65, 22.50, 13.92; MS 489 (M+NH$_4^+$).

The disclosure of each patent, patent application and publication cited or described in the specification is hereby incorporated by reference herein in its entirety.

Although the invention has been set forth in detail, one skilled in the art will appreciate that numerous changes and modifications can be made to the invention without departing from the spirit and scope thereof.

What is claimed is:

1. A compound of formula (I) or a pharmaceutically acceptable salt thereof, wherein the compound of formula (I) is:

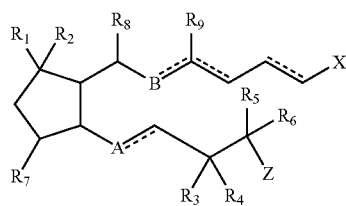

(I)

wherein the dotted lines indicate a single or a double bond;
R$_1$ is —OD$_1$ or —Cl;
R$_2$ and R$_8$ are a hydrogen; or R$_1$ and R$_2$ taken together are =CH$_2$ or =O;
R$_3$ and R$_4$ are each independently a hydrogen, —OD, or —CH$_3$;
R$_5$ and R$_6$ are each independently a hydrogen, —OD$_1$, —CH$_3$, —OCH$_3$ or —CH=CH$_2$;
R$_7$ is a hydrogen or —OD$_1$;
R$_9$ is hydrogen or absent when the carbon to which it is attached is the central carbon of an allene functionality; or R$_8$ and R$_9$ taken together with the chain to which they are attached form a substituted benzene ring;
A is —CH=, —CH$_2$, —S—, or —O—;
B is —CH=, —CH$_2$, —S—, or —C(O)—;
X is —CH$_2$OR$_{11}$, —C(O)OR$_{11}$ or —C(O)N(D$_1$)R$_{12}$;
R$_{11}$ is D$_1$, a lower alkyl group, or

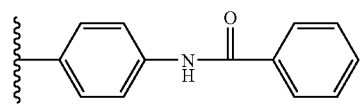

R$_{12}$ is —S(O)$_2$CH$_3$ or —C(O)CH$_3$;
Z is (a) an ethyl, (b) a butyl, (c) a hexyl, (d) a benzyl,

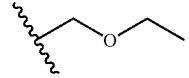
(e)

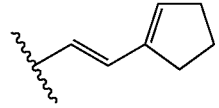
(f)

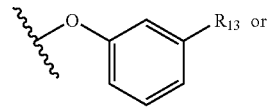
(g)

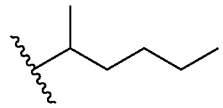
(b)

R$_{13}$ is a hydrogen or —Cl;
D$_1$ is a hydrogen or D; with the proviso that at least one D$_1$ in formula (I) must be D;
D is Q or K;
Q is —NO or —NO$_2$;
K is —W$_a$—E$_b$—(C(R$_e$)(R$_f$))$_p$—E$_c$—(C(R$_e$)(R$_f$))$_n$—W$_d$—(C(R$_e$)(R$_f$))$_y$—W$_i$—E$_j$—W$_g$—(C(R$_e$)(R$_f$))$_z$—T—Q;
a, b, c, d, g, i and j are each independently an integer from 0 to 3;
p, x, y and z are each independently an integer from 0 to 10;
W at each occurrence is independently —C(O)—, —C(S)—, —T—, —(C(R$_e$)(R$_f$))$_h$—, an alkyl group, an aryl group, a heterocyclic ring, an arylheterocyclic ring, or —(CH$_2$CH$_2$O)$_q$—;
E at each occurrence is independently —T—, an alkyl group, an aryl group, —(C(R$_e$)(R$_f$))$_h$—, a heterocyclic ring, an arylheterocyclic ring, or —(CH$_2$CH$_2$O)$_q$—;
h is an integer form 1 to 10;
q is an integer from 1 to 5;
R$_e$ and R$_f$ are each independently a hydrogen, an alkyl, a cycloalkoxy, a halogen, a hydroxy, an hydroxyalkyl, an alkoxyalkyl, an arylheterocyclic ring, an alkylaryl, a cycloalkylalkyl, a heterocyclicalkyl, an alkoxy, a haloalkoxy, an amino, an alkylamino, a dialkylamino, an arylamino, a diarylamino, an alkylarylamino, an alkoxyhaloalkyl, a haloalkoxy, a sulfonic acid, a sulfonic ester, an alkylsulfonic acid, an arylsulfonic acid, an arylalkoxy, an alkylthio, an arylthio, a cycloalkylthio, a cycloalkenyl, a cyano, an aminoalkyl, an aminoaryl, an aryl, an arylalkyl, an alkylaryl, a carboxamido, a alkylcarboxamido, an arylcarboxamido, an amidyl, a carboxyl, a carbamoyl, a carbamate, an alkylcarboxylic acid, an arylcarboxylic acid, an alkylcarbonyl, an arylcarbonyl, an ester, a carboxylic ester, an alkylcarboxylic ester, an arylcarboxylic ester, a haloalkoxy, a sulfonamido, an alkylsulfonamido, an arylsulfonamido, a sulfonic ester, a urea, a phosphoryl, a nitro, —T—Q, or R$_e$ and R$_f$ are —(C(R$_e$)(R$_f$))$_k$—T—Q, wherein R$_e$ and R$_f$ are as defined herein, or R$_e$ and R$_f$ taken together with the carbons to which they are attached form a carbonyl, a methanthial, a heterocyclic ring, a cycloalkyl group or a bridged cycloalkyl group;
k is an integer from 1 to 3;

T at each occurrence is independently a covalent bond, a carbonyl, an oxygen, —S(O)O— or —N($R_a$)$R_i$—;

o is an integer from 0 to 2;

$R_a$ is a lone pair of electrons, a hydrogen or an alkyl group;

$R_i$ is a hydrogen, an alkyl, an aryl, an alkylcarboxylic acid, an arylcarboxylic acid, an alkylcarboxylic ester, an arylcarboxylic ester, an alkylcarboxamido, an arylcarboxamido, an alkylaryl, an alkylsulfinyl, an alkylsulfonyl, an arylsulfinyl, an arylsulfonyl, a sulfonamido, a carboxamido, a carboxylic ester, an amino alkyl, an amino aryl, —$CH_2$—C(T—Q)($R_e$)($R_f$), or —($N_2O_2$—)⁻.$M^+$, wherein $M^+$ is an organic or inorganic cation; with the proviso that when $R_i$ is —$CH_2$—C(T—Q)($R_e$)($R_f$) or —($N_2O_2$)⁻.$M^+$, or $R_e$ or $R_f$ are T—Q or $R_e$ and $R_f$ are —(C($R_e$)($R_f$))$_k$—T—Q, wherein $R_e$ and $R_f$ are as defined herein, then the "—T—Q" subgroup can be a hydrogen, an alkyl, an alkoxy, an alkoxyalkyl, an aminoalkyl, a hydroxy, a heterocyclic ring or an aryl group;

with the proviso that the compound of formula (I) has at least one NO group or at least three $NO_2$ groups linked through an oxygen atom, a nitrogen atom or a sulfur atom.

2. The compound of claim 1, wherein the compound of formula (I) is a nitrosated arbaprostil, a nitrosylated arbaprostil, a nitrosated and nitrosylated arbaprostil, a nitrosated alprostadil, a nitrosylated alprostadil, a nitrosated and nitrosylated alprostadil, a nitrosated carboprost, a nitrosylated carboprost, a nitrosated and nitrosylated carboprost, a nitrosated cloprostenol, a nitrosylated cloprostenol, a nitrosated and nitrosylated cloprostenol, a nitrosated dimoxaprost, a nitrosylated dimoxaprost, a nitrosated and nitrosylated dimoxaprost, a nitrosated enprostil, a nitrosylated enprostil, a nitrosated and nitrosylated enprostil, a nitrosated enisoprost, a nitrosylated enisoprost, a nitrosated and nitrosylated enisoprost, a nitrosated fenprostalene, a nitrosylated fenprostalene, a nitrosated and nitrosylated fenprostalene, a nitrosated gemeprost, a nitrosylated gemeprost, a nitrosated and nitrosylated gemeprost, a nitrosated latanoprost, a nitrosylated latanoprost, a nitrosated and nitrosylated latanoprost, a nitrosated meteneprost, a nitrosylated meteneprost, a nitrosated and nitrosylated meteneprost, a nitrosated mexiprostil, a nitrosylated mexiprostil, a nitrosated and nitrosylated mexiprostil, a nitrosated misoprostol, a nitrosylated misoprostol, a nitrosated and nitrosylated misoprostol, a nitrosated misoprostol acid, a nitrosylated misoprostol acid, a nitrosated and nitrosylated misoprostol acid, a nitrosated nocloprost, a nitrosylated nocloprost, a nitrosated and nitrosylated nocloprost, a nitrosated omoprostil, a nitrosylated omoprostil, a nitrosated and nitrosylated omoprostil, a nitrosated prostalene, a nitrosylated prostalene, a nitrosated and nitrosylated prostalene, a nitrosated $PGE_1$, a nitrosylated $PGE_1$, a nitrosated and nitrosylated $PGE_1$, a nitrosated $PGE_2$, a nitrosylated $PGE_2$, a nitrosated and nitrosylated $PGE_2$, a nitrosated $PGF_1$, a nitrosylated $PGF_1$, a nitrosated and nitrosylated $PGF_1$, a nitrosated $PGF_{2\alpha}$, a nitrosylated $PGF_{2\alpha}$, a nitrosated and nitrosylated $PGF_{2\alpha}$, a nitrosated rioprostil, a nitrosylated rioprostil, a nitrosated and nitrosylated rioprostil, a nitrosated rosaprostol, a nitrosylated rosaprostol, a nitrosated and nitrosylated rosaprostol, a nitrosated remiprostol, a nitrosylated remiprostol, a nitrosated and nitrosylated remiprostol, a nitrosated sulprostone, a nitrosylated sulprostone, a nitrosated and nitrosylated sulprostone, a nitrosated trimoprostil, a nitrosylated trimoprostil, a nitrosated and nitrosylated trimoprostil, a nitrosated tiprostamide, a nitrosylated tiprostamide, a nitrosated and nitrosylated tiprostamide, a nitrosated unoprostone, or a nitrosylated unoprostone, a nitrosated and nitrosylated unoprostone.

3. A composition comprising the compound of claim 1 and a pharmaceutically acceptable carrier.

4. A nitrosylated arbaprostil, a nitrosylated alprostadil, a nitrosylated carboprost, a nitrosylated cloprostenol, a nitrosylated dimoxaprost, a nitrosylated enprostil, a nitrosylated enisoprost, a nitrosylated fenprostalene, a nitrosylated gemeprost, a nitrosylated latanoprost, a nitrosylated meteneprost, a nitrosylated mexiprostil, a nitrosylated misoprostol, a nitrosylated misoprostol acid, a nitrosylated nocloprost, a nitrosylated ornoprostil, a nitrosylated prostalene, a nitrosylated $PGE_1$, a nitrosylated $PGE_2$, a nitrosylated $PGF_1$, a nitrosylated $PGF_{2\alpha}$, a nitrosylated rioprostil, a nitrosylated rosaprostol, a nitrosylated remiprostol, a nitrosylated sulprostone, a nitrosylated trimoprostil, a nitrosylated tiprostanide, a nitrosylated unoprostone, or a pharmaceutically acceptable salt thereof, comprising at least one NO group; wherein the at least one NO group is linked to the arbaprostil, alprostadil, carboprost, cloprostenol, dimoxaprost, enprostil, enisoprost, fenprostalene, gemeprost, latanoprost, meteneprost, mexiprostil, misoprostol, misoprostol acid, nocloprost, ornoprostil, prostalene, $PGE_1$, $PGE_2$, $PGF_1$, $PGF_{2\alpha}$, rioprostil, rosaprostol, remiprostol, sulprostone, trimoprostil, tiprostanide or unoprostone, through an oxygen atom, a nitrogen atom or a sulfur atom.

* * * * *